United States Patent
Vielhaber et al.

(10) Patent No.: US 9,060,943 B2
(45) Date of Patent: Jun. 23, 2015

(54) COMPOSITIONS COMPRISING TRANS-TERT-BUTYL CYCLOHEXANOL AS SKIN IRRITATION-REDUCING AGENT

(75) Inventors: Gabriele Vielhaber, Paris (FR); Heiko Oertling, Holzminden (DE); Claudia Gömann, Warbsen (DE); Antje Köhler, Holzminden (DE); Michael Krohn, Lorsch (DE); Holger Zinke, Heppenheim (DE)

(73) Assignee: SYMRISE AG, Holzminden (DE)

( * ) Notice: Subject to any disclaimer, the term of this patent is extended or adjusted under 35 U.S.C. 154(b) by 345 days.

(21) Appl. No.: 13/263,016

(22) PCT Filed: Apr. 9, 2009

(86) PCT No.: PCT/EP2009/054336
§ 371 (c)(1),
(2), (4) Date: Dec. 30, 2011

(87) PCT Pub. No.: WO2009/087242
PCT Pub. Date: Jul. 16, 2009

(65) Prior Publication Data
US 2012/0121737 A1    May 17, 2012

(51) Int. Cl.
| | | |
|---|---|---|
| A61K 8/34 | (2006.01) |
| A23C 9/13 | (2006.01) |
| A23C 11/10 | (2006.01) |
| A23L 1/30 | (2006.01) |
| A23L 2/02 | (2006.01) |
| A23L 2/39 | (2006.01) |
| A61K 8/02 | (2006.01) |
| A61K 31/045 | (2006.01) |
| A61K 45/06 | (2006.01) |
| A61Q 5/02 | (2006.01) |
| A61Q 11/00 | (2006.01) |
| A61Q 15/00 | (2006.01) |
| A61Q 17/04 | (2006.01) |
| A61Q 19/00 | (2006.01) |
| A61Q 19/02 | (2006.01) |
| A61Q 19/04 | (2006.01) |

(52) U.S. Cl.
CPC .................. *A61K 8/34* (2013.01); *A23C 9/1307* (2013.01); *A23C 11/103* (2013.01); *A23L 1/30* (2013.01); *A23L 2/02* (2013.01); *A23L 2/39* (2013.01); *A61K 8/0216* (2013.01); *A61K 8/0229* (2013.01); *A61K 31/045* (2013.01); *A61K 45/06* (2013.01); *A61K 2800/75* (2013.01); *A61K 2800/874* (2013.01); *A61K 2800/92* (2013.01); *A61Q 5/02* (2013.01); *A61Q 11/00* (2013.01); *A61Q 15/00* (2013.01); *A61Q 17/04* (2013.01); *A61Q 19/004* (2013.01); *A61Q 19/005* (2013.01); *A61Q 19/02* (2013.01); *A61Q 19/04* (2013.01)

(58) Field of Classification Search
CPC ....... A61Q 19/02; A61Q 17/04; A61Q 15/00; A61Q 11/00; A61Q 19/004; A61Q 19/005; A61Q 19/04; A61Q 19/06; A61Q 19/08; A61Q 5/02; A61Q 13/00; A61Q 17/00; A61Q 19/00; A61Q 1/02; A61Q 5/00
See application file for complete search history.

(56) References Cited

U.S. PATENT DOCUMENTS

| 2,927,127 | A |   | 3/1960 | Somerville et al. |
|---|---|---|---|---|
| 5,540,853 | A | * | 7/1996 | Trinh et al. .................... 510/101 |
| 5,858,958 | A |   | 1/1999 | Holzner |
| 6,027,668 | A |   | 2/2000 | Holzner |
| 2007/0021319 | A1 | * | 1/2007 | Kohle et al. ........................ 512/2 |

FOREIGN PATENT DOCUMENTS

| CN | 1175900 A | 3/1998 |
|---|---|---|
| CN | 1188098 A | 7/1998 |
| EP | 0755910 | 1/1997 |
| JP | S5929618 A | 2/1984 |
| JP | H11501081 A | 1/1999 |
| JP | 2004107208 A | 4/2004 |
| WO | WO 97/22332 | 6/1997 |
| WO | WO-9722332 A1 | 6/1997 |
| WO | WO-2007042472 A1 | 4/2007 |
| WO | WO 2008/117254 | 10/2008 |

OTHER PUBLICATIONS

Symrise GmbH & Co. KG, "Trans-tert-butyl cyclohexanol as skin irritation-reducing agent," Research Disclosure, Mason Publications, vol. 542, No. 17, Jun. 1, 2009, p. 595, XP007139063.
Notification of the First Office Action, Chinese Application No. 200980159616.0, issued Nov. 15, 2012 (English Translation).
International Search Report and Written Opinion of the International Searching Authority for PCT/EP2009/054336 sent Aug. 1, 2010.
Second Office Action, Chinese Application No. 200980159616.0, issued by the State Intellectual Property Office (SIPO) on Apr. 17, 2013, together with the reporting letter from the Chinese patent associates.
Office Action from the Japanese Patent Office issued in parallel Japanese Application No. 2012-503873 together with the English translation, received on Nov. 25, 2013.
Office Action from the Japanese Patent Office issued in parallel Japanese Application No. 2012-503873 together with the English translation, on Dec. 22, 2014.

* cited by examiner (Continued)

Primary Examiner — Terry A. McKelvey
Assistant Examiner — Catheryne Chen
(74) Attorney, Agent, or Firm — Novak Druce Connolly Bove + Quigg LLP

(57) ABSTRACT

The present invention primarily relates to the use of trans-tert-butyl cyclohexanol as skin irritation-reducing agent as well as compositions (formulations) having a skin irritation-reducing action comprising trans-tert-butyl cyclohexanol as skin irritation-reducing agent.

19 Claims, No Drawings

COMPOSITIONS COMPRISING TRANS-TERT-BUTYL CYCLOHEXANOL AS SKIN IRRITATION-REDUCING AGENT

CROSS-REFERENCE TO RELATED APPLICATIONS

This application is a National Phase filing under 35 U.S.C. §371 of PCT/EP2009/054336, filed Apr. 9, 2009, the entire contents of which is incorporated herein by reference.

The present invention primarily relates to the use of trans-4-tert-butyl cyclohexanol as skin irritation-reducing (soothing) agent as well as compositions (formulations) and products having a skin irritation-reducing (soothing) action comprising trans-4-tert-butyl cyclohexanol as skin irritation-reducing agent.

It also relates to a medicament (pharmaceutical composition) for treatment of skin irritations and/or pain conditions and the use of such a formulation or of such a medicament for prophylaxis (prevention) of skin irritation and/or treatment of skin irritations for medical and/or other than medical, in particular cosmetic, purposes.

In some subjects, especially humans with sensitive skin, certain substances may cause skin irritation, said skin irritation being perceived as a stinging effect or burning sensation if the substance applied on the skin, especially on the face. Examples of such substances used in the field of cosmetics are skin lighteners, skin tanning agents, antibacterial agents, anti-dandruff agents, antiacne agents, compounds against ageing of the skin, emulsifiers, detergents, deodorizing agents, antiperspirants, skin warming agents, hair removing agents, abrasives, anti-cellulite agents or certain classes of chemical compounds, e.g. phenol derivatives or $\alpha$-hydroxy acids.

Thus, the present invention moreover relates to a process for the preparation of a formulation or of a medicament (pharmaceutical composition) having a skin irritation-reducing action, a cosmetic or therapeutic method for prophylaxis (prevention) of skin irritations, a cosmetic or therapeutic method for treatment of skin irritations, a method for prophylaxis of the skin-irritating action and a method for reducing, eliminating or suppressing the skin-irritating action of a substance or substance mixture able to cause skin irritation.

In the cosmetics and pharmaceuticals industry, there is a constant need for agents having a skin irritation-reducing action.

The skin, in particular the epidermis, as a barrier organ of the human organism is subjected to external influences to a particular extent. Many intrinsic (e.g. genetic predisposition) and extrinsic (e.g. damage to the skin barrier, action of UV light, irritating or allergy-inducing substances) factors can lead to skin irritation. In connection with this invention, skin irritation is to be understood as meaning any change to the skin which induces sensorial malaise in humans and/or is characterized by the symptoms a dry, reddened and/or inflamed skin. The term sensorial malaise here also includes states such as pain. Skin irritation can include, in particular, phenomenologically different skin states: delicate skin, sensitive skin, including sensitive scalp, easily injured skin, atopic skin, irritated skin or inflamed skin, which manifests itself in an in each case higher severity in a reddening of the skin, so-called erythema.

The problem of "delicate skin" affects a growing number of adults and children. It is now assumed that up to 50% of the population have a delicate skin.

Sensitive skin is one of the most common disturbing skin conditions and can have high influence on life quality. The prevalence for self-declared sensitive skin had been reported to be about 50% in the EU, USA and Japan and 36% in China.

People having sensitive skin for example observe facial discomfort with burning, stinging and similar skin sensation. Sensitive skin can be caused by rapid changes in temperature, wind or by some cosmetics. It clearly is a neurological phenomenon not correlating with allergic hypersensitivity or atopic dermatitis. People having sensitive skin often show an enhanced density of TRPV1 receptors on skin nerves and a higher sensitivity towards capsaicin is also frequently observed (which decreases with age due to decrease of skin ennervation).

Delicate skin describes a skin having a reduced irritation threshold for irritants, such as hyper-reactive and intolerant, and also atopic skin. In the case of humans with delicate, sensitive or easily injured skin, a phenomenon called "stinging" ("to sting"=becoming injured, burn, be painful) can be observed. Typical adverse phenomena associated with the terms "stinging" or "sensitive skin" are reddening of the skin, tingling, prickling, skin tightness and burning of the skin. They can be caused by stimulating environmental conditions, such as e.g. massage, action of surfactants, influence of weather, such as heat, cold, dryness and also damp heat, thermal radiation and UV radiation, e.g. from the sun, or psychological stress.

A "sensitive" scalp is likewise characterized by reddening of the skin, tingling, prickling, burning. Triggers are, for example, soap, shampoos or other hair care compositions, surfactants, hard water having high lime concentrations and/or mechanical stress. Erythemas and hyperseborrhoea (excessive production of sebum) of the scalp and dandruff are often associated with the phenomena described.

In about 10-20% of the population of industrial countries, with an increasing trend, atopy is to be observed, a hypersensitivity, of familial origin, of the skin and mucous membranes to environmental substances with an increased readiness to develop hypersensitivity reactions of the immediate type (allergies) to substances from the natural environment. Atopy is presumed to be of genetic origin. Atopy can manifest itself as atopic dermatitis. In this case, the skin barrier is damaged and the skin is often inflamed.

The erythematous action of the ultraviolet part of sunlight or artificial radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even more or less severe burns.

Erythematous skin symptoms also occur as concomitant symptoms with certain skin diseases or irregularities. For example, the typical skin rash of the symptoms of acne is regularly reddened to a greater or lesser degree and impairs the well-being of those affected even in mild cases.

Erythemas also occur to an increased extent in the nappy region of infants, and all the more so of babies (nappy dermatitis). Incontinence, a condition which occurs to an increased extent especially in old age, is also often associated with erythemas and reddening of the skin as a consequence of continual exposure to moisture and irritants (incontinence dermatitis).

A large number of active compounds having a skin irritation-reducing action are indeed already employed in the technical fields referred to, but alternatives nevertheless continue to be sought. In the connection with this invention skin irritation-reducing action is to be understood as meaning the moderation, reduction, elimination or prevention of skin irritations, in particular that of the skin symptoms described above. The skin irritation-reducing action here is based in particular on soothing of the skin, inhibition of inflammation and/or alleviation of reddening. In this text, the term "skin" also includes the term "mucous membrane". In the search for alternative agents, however, it should be remembered that the substances used must be toxicologically acceptable, tolerated well by the skin and stable (in particular in the conventional cosmetic and/or pharmaceutical formulations), should have the lowest possible intrinsic odour and the lowest possible intrinsic colour and must be inexpensive to prepare. In accordance with the persistent trend towards natural active compounds, novel active compounds of natural, in particular plant origin are sought in particular.

Persons skilled in the art have already addressed the problem of skin irritation and have described, e.g. the skin irritation-reducing properties of bisabolol and of ginger (Zingiber officinale) extract. WO 2007/042472 discloses mixtures of ginger extract or the compounds contained in ginger extract with bisabolol having a significantly improved, synergistic, skin irritation-reducing action compared with the components used individually.

Capsaicin is a natural agonist of the Transient Receptor Potential V1 (TRPV1, vanilloid receptor, VR1). TRPV1 is expressed on central and peripheral neurons. Different types of stimuli activate the receptor such as low pH (<5.9), noxious heat (>42° C.), the cannabinoid/endovanilloid anandamide, leukotriene B4 and exogenous capsaicin. As a result e.g. after capsaicin application, TRPV1 is stimulated to either transmit burning pain or a burning pruritus. Moreover, the TRPV1 receptor may be sensitized by bradykinin and prostaglandins, as well as by Nerve Growth Factor, with lowering of the activation threshold and facilitated induction of pain. Due to the sensory function of TRPV1 (burning pain, burning pruritus), it may be speculated that the TRPV1 is involved in sensitive skin.

TRPV1 is also expressed in many non-neuronal cells, among them keratinocytes, differentiated sebocytes, hair follicle cells, sweat gland ducts, the secretory portion of eccrine sweat glands, mast cells and 3T3-L1-preadipocytes and fibroblasts. TRPV1 activation in keratinocytes by capsaicin or heat causes the release of inflammatory mediators such as PGE2 (prostaglandin E2) and IL-8 (interleukin-8), and induction of matrix metalloproteinases such as MMP-1, respectively.

In this context "antagonistic activity" refers to a pharmaceutical and/or cosmetic active inhibition of the TRPV1 related bioactivity. An antagonistically effective amount means an amount sufficient to modulate, and preferably reduce by at least about 30 percent, more preferably at least 50 percent, most preferably by at least 80 percent, the TRPV1 receptor activity, preferably measured as described in Example 1.1.

An object of the present invention was therefore to provide a component which has a, preferably improved, skin irritation-reducing action, in particular for reducing or alleviating one or more skin sensations from the group consisting of stinging, burning, tingling, tickling and skin tightness.

This object is achieved by using trans-4-tert-butyl cyclohexanol as skin irritation-reducing agent, in particular for
a) reducing or alleviating one or more human skin sensations from the group consisting of stinging, burning, tingling, tickling and skin tightness,
b) as a TRPV1 antagonist, or
c) for preparing a cosmetical or pharmaceutical composition for the treatment or prevention of skin irritation.

Trans-4-tert-butyl cyclohexanol used in accordance with the present invention can also be applied as part of a medicament (pharmaceutical composition), especially for treating pain conditions, mediated by the vanilloid receptor TRPV1.

In the context of the present invention, the term "trans-4-tert-butyl cyclohexanol" here includes (+)-trans-4-tert-butyl cyclohexanol, (−)-trans-4-tert-butyl cyclohexanol, represented by the following formulae, and mixtures thereof.

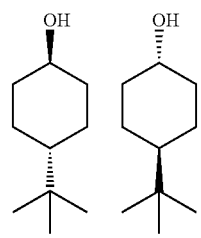

In particular, the term "trans-4-tert-butyl cyclohexanol" includes the racemic mixture of (+)-trans- and (−)-trans 4-tert-butyl cyclohexanol.

The present invention also relates to a (preferably topical) cosmetic composition having a skin irritation-reducing action consisting of or comprising:
a) 0.1-4.5 wt. %, preferably 0.25-4.0 wt. %, more preferably 0.375-3.0 wt. %, even more preferably 0.5-2.5 wt. %, most preferably 0.6-2 wt. %, of trans-4-tert-butyl cyclohexanol or a cosmetically or pharmaceutically acceptable salt thereof, in particular the $Na^+$, $K^+$, $NH_4^+$, $Mg^{2+}$ or $Ca^{2+}$ salt, based on the total weight of the composition, and
b) one or more cosmetically acceptable carriers, preferably a cosmetically acceptable carrier other than water or ethanol.

The weight percentages of trans-4-tert-butyl cyclohexanol are understood to refer to the total of the (+) and (−) isomers, respectively, if so present. Thus, for example, if no (−) isomer is present, the weight percentage refers to the (+) isomer, and if both isomers are present, refers to the total amount of both isomers.

The compositions according to the present invention, in particular topical cosmetic compositions, are particularly suitable for reducing skin irritation, in particular for soothing the skin and/or reducing or alleviating one or more skin sensations from the group consisting of stinging, burning, tingling, tickling and skin tightness, more particularly stinging and burning.

The compound used in the context of the present invention, trans-4-tert-butyl cyclohexanol, is as such known in the prior art.

U.S. Pat. No. 2,927,127 discloses that hydrogenation of p-tert-butyl phenol with a Ni catalyst yields p-tert-butyl cyclohexanol having proportions of approximately 30% cis-isomer and approximately 70% trans-isomer. U.S. Pat. No. 2,927,127 further describes the hydrogenation of p-tert-butyl phenol using Rh/C as catalyst in ethanol to yield p-tert-butyl cyclohexanol containing 87.5% of the cis-isomer, which was subsequently converted to the corresponding acetates by reaction with acetic anhydride.

U.S. Pat. No. 5,160,498 describes the hydrogenation of p-tert-butyl phenol or p-tert-butyl cyclohexanone using a $BF_3$-modified Rh catalyst in solvents like cyclohexane or tetrahydrofuran to yield p-tert-butyl cyclohexanol containing more than 80% of the cis-isomer EP 0 755 910 relates to a process for preparing 4-tert-butyl cyclohexanol predominantly containing the cis-isomer by hydrogenation of p-tert-butyl phenol. The hydrogenations according to EP 0 755 910 can be carried out in various solvents, e.g. alkanes, cyclic alkanes, acyclic ethers or alcohols like ethanol, iso-propanol or 4-methyl-2-pentanol are mentioned.

JP 61-263944 A discloses the preparation of 1-allyloxy-4-tert-butylcyclohexane by adding allyl bromide to a mixture of tetra-n-butylammonium bisulphate, 4-tert-butylcyclohexanol (cis:trans ratio=28:72), n-hexane and a 50 wt-% aqueous solution of NaOH.

Highly pure trans-4-tert-butyl cyclohexanol can be obtained as described in Organic Syntheses Collective Volume 5, 175-178, Wiley, New York, 1973, by reduction of p-tert-butyl cyclohexanone with $LiAlH_4$ and $AlCl_3$. Recrystallization from petroleum ether yields essentially pure trans-4-tert-butyl cyclohexanol (purity >99 wt. %).

According to J. Am. Chem. Soc. 1955, 77, 5562-5578 the pure trans-isomer of 4-tert-butyl cyclohexanol is also obtainable from commercially available mixtures of 4-tert-butyl cyclohexanol-isomers via repeated crystallization of the acid phthalate followed by saponification of the corresponding pure trans ester with sodium hydroxide in water and subsequent extraction with pentane. The pure trans-isomer of 4-tert-butyl cyclohexanol was also obtained by chromatography over activated alumina starting from a mixture of 4-tert-butyl cyclohexanols having a content of the trans-isomer of about 61%.

JP 08-012620-A describes the conversion of 4-tert-butyl-cyclohexanol (cis:trans ratio=25:75) into esters, preferably the pivalate or benzoate, e.g. via transesterification with methyl pivalate or methyl benzoate in toluene in the presence of a titanate catalyst (e.g. tetrabutyl titanate). Subsequently the 4-tert-butylcyclohexanol esters were obtained by crystallization.

U.S. Pat. No. 2,582,743 states that p-tert-butyl cyclohexanol has a musty camphorlike smell. No information is given regarding the proportion of the cis- and/or trans-isomer.

U.S. Pat. No. 5,858,958 mentions that p-tert-butyl cyclohexanol is a known perfumery ingredient which is not very currently used in perfumery due to its not too elegant camphoraceous note.

Steffen Arctander describes 4-tert-butyl cyclohexanol in "Perfume and Flavor Chemicals", private publication, Montclair, N.J., 1969, entry 433, as having an extremely dry, woody-camphoraceous odour with leather-like undertones which can used in artificial patchouli oils and to lend power, diffusiveness and radiance to soap fragrances. No information is given regarding the cis- and/or trans-isomer ratio.

When used as commercially available (fragrance) material 4-tert-butyl cyclohexanol essentially consists of the trans-isomer and the cis-isomer, the weight-ratios being in the range from about 68:32 to about 73:27.

GB 1,580,184 discloses a fragrance mixture in form of a patchouli base comprising about 4.9 wt. % of p-tert-butyl cyclohexanol. No information is given regarding the cis- and/or trans-isomer content of the p-tert-butylcyclohexanol used therein.

U.S. Pat. No. 6,566,562 uses p-tert-butyl cyclohexanol at a level of 3.25 wt. % in a perfume oil having natural patchouli character. No information is given regarding the cis- and/or trans-isomer content of the p-tert-butylcyclohexanol used therein.

WO 2008/117254 describes a perfuming composition of the patchouli type comprising p-tert-butyl cyclohexanol in an amount of 12.94 wt. %. Said perfuming composition contains dipropylene glycol at a level of 7.09 wt. %, based on the total weight of said perfuming composition. No information is given regarding the cis- and/or trans-isomer content of the p-tert-butylcyclohexanol used therein.

U.S. Pat. No. 5,858,958 relates to the use of 4-tert-butyl cyclohexanol as antioxidant, in particular as stabilizing agent against oxidation in cleaning or cosmetic products. Improved antioxidative results were observed when 4-tert-butyl cyclohexanol was combined with tocopherols (alpha- or gamma-), citric acid, ascorbic acid or tartaric acid or their esters. Preferred amounts in cosmetic skin or hair cleaning compositions indicated are 0.05 to 0.5 wt. % and in perfume compositions 0.5 to 50 wt. %, in both cases based on the total weight of the composition. The examples disclose cosmetic products like soap, shampoo, and all-purpose cleaner with a content of 4-tert-butyl cyclohexanol of from 0.1 to 0.2 wt. %. Further disclosed therein is a perfume oil comprising 10 wt. % of p-tert-butyl cyclohexanol which was incorporated into a soap base resulting in amounts of 0.15 to 0.2 wt. % of 4-tert-butyl cyclohexanol in the final soap. However, U.S. Pat. No. 5,858,958 is overall silent regarding the cis- and/or trans-isomer content of the 4-tert-butylcyclohexanol used therein.

Preferably, a (topical) formulation according to the present invention comprising trans-4-tert-butyl cyclohexanol or a cosmetically or pharmaceutically acceptable salt thereof is suitable for topical application on human skin, preferably used for application in the region of the head.

Cosmetic formulations for application in the region of the head are, in particular, those which may come into contact with the oral cavity even when applied properly to the skin, for example—cosmetic cleansing or care compositions for the face region, face creams or lotions or ointments, sunscreen compositions, lipsticks or other lip cosmetics or lip care compositions.

An "skin effective amount" in the context of the present invention refers to an amount effective to reduce or alleviate skin irritation and/or to avoid skin irritation of human skin, in particular regarding one or more skin sensations from the group consisting of stinging, burning, tingling, tickling and tightness.

In one embodiment of the present invention, the (topical) formulation conventionally comprises one or more substances able to cause skin irritation of human skin, in particular one or more skin sensations from the group consisting of stinging, burning, tingling, tickling and skin tightness.

The invention also provides a medicament (pharmaceutical compositions), preferably for treatment of skin irritations and/or for treating pain conditions, comprising trans-4-tert-butyl cyclohexanol in an amount having an irritation- and/or pain-reducing action. Such a medicament can be employed in the field of human medicine against a large number of pains and diseases, such as, for example, urticaria, contact dermatitis, atopy and generally all inflammation processes, included tooth and gum inflammations, such as parodontosis.

The pure cis-isomer and the pure trans-isomer of racemic 4-tert-butyl cyclohexanol were tested separately for TRPV1 antagonism at parallel application with capsaicin as agonist. It was found that the pure trans-isomer was significantly more active than a 50/50 mixture of cis- and trans-isomer, whereas the pure cis-isomer was inactive.

In the process of making the present invention the pure cis- and trans-isomers of 4-tert-butyl cyclohexanol were tested separately in a pre-incubation mode with application of the respective isomer 10 min before addition of the agonist capsaicin. Also this experiment showed strong activity of trans-4-tert-butyl cyclohexanol, also here the cis-isomer was not active.

Based on these results and the in vivo data summarized below in Example 1.2, the inventors conclude that trans-4-tert-butyl cyclohexanol is a very effective, highly specific TRPV1 antagonist in vitro as well as in vivo. Moreover, only the trans-isomer of 4-tert-butyl cyclohexanol was shown to be the bioactive, TRPV1 antagonizing isomer.

In addition, the cis-isomer has a marked, unpleasant earthy odour which was clearly stronger than that of the trans-isomer and which was clearly perceivable at a dosage of 1 wt. % in a non-perfumed cosmetic composition. This odour makes the cis-isomer far less suitable for (topical) cosmetic formulations at higher dosages, in particular at use level above 0.3 wt. %, based on the total weight of the cosmetic composition. It was also found that the trans-isomer exhibits only a weak odour which is not or only slightly perceivable at a dosage of 1 wt. % in a non-perfumed cosmetic composition.

Thus, in preferred compositions according to the present invention the weight ratio of trans-4-tert-butyl cyclohexanol (that is: the total of all respective trans-isomers) to cis-4-tert-butyl cyclohexanol (that is: the total of all respective cis-isomers), if present, is 75:25 or greater, preferably greater than 80:20, more preferably greater than 90:10, most preferably greater than 95:5.

It was further observed by the inventors that trans-4-tert-butyl cyclohexanol is a solid at 20° C. having a pronounced sublimation behaviour. In addition, it has a tendency to (re-)crystallize out of (topical) cosmetic compositions and products, in particular at levels of 0.5 wt. % and above. This makes trans-4-tert-butyl cyclohexanol rather difficult to handle and to store, in particular in (topical) cosmetic compositions and products, in particular those comprising water in an amount of 10 wt. % or more, based on the total weight of the formulation or product, or comprising a water and an oil phase (e.g. O/W— or W/O-emulsions).

Without wishing to be bound by theory, it is assumed by the inventors that the combinations of the cosmetically acceptable carriers and fragrance materials mentioned below (in particular those with higher C log P values) reduce the vapour pressure of trans-4-tert-butyl cyclohexanol and thereby improve the sublimation behaviour of trans-4-tert-butyl cyclohexanol. These cosmetically acceptable carriers and fragrance materials thereby "trap" and hold the trans-4-tert-butyl cyclohexanol within the (topical) cosmetic compositions and products.

Further, it was also found by the inventors that the (preferred) cosmetically acceptable carriers and fragrance materials mentioned (in particular those with higher C log P values) improve or even avoid the tendency of trans-4-tert-butyl cyclohexanol to (re-)crystallize out of (topical) cosmetic compositions.

Preferred formulations and products according to the invention comprising (preferred) cosmetically acceptable carriers and fragrance materials mentioned (in particular those with higher C log P values) were found to have improved stability (regarding the sublimation and/or (re-)crystallization properties of trans-4-tert-butyl cyclohexanol), in particular in (topical) cosmetic composition and products, in particular those comprising water (preferably in an amount of 10 to 95 wt. %, more preferably 25 to 90 wt. %, even more preferably 40 to 90 wt. %, in each case based on the total weight of the composition or product), and in (topical) cosmetic composition and products comprising water and an oil phase (e.g. O/W or W/O-emulsions).

The present invention thus also relates to a concentrated composition comprising or consisting of 5 to 55 wt. %, preferably 15-40 wt. %, of trans-4-tert-butyl cyclohexanol, based on the total weight of the composition, -one or more diols, preferably alkane diol(s), having 3 to 10 carbon atoms, preferably in a total amount of 7.5 wt. % or more, more preferably at least 12.5 wt. %, even more preferably 25 to 95 wt. %, most preferably in a total amount of at least 40 wt. % and most preferred in a total amount of 60 to 85 wt. %, and which are preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, dipropylene glycol, preferably 1,2-butylene glycol, 1,2-pentanediol and/or dipropylene glycol, wherein, optionally and preferably, the weight ratio as described above of trans-4-tert-butyl cyclohexanol to cis-4-tert-butyl cyclohexanol, if present, is 75:25 or greater, preferably greater than 80:20, more preferably greater than 90:10, most preferably greater than 95:5.

These compositions are easy to handle and stable over a prolonged period of time (even at lower temperatures of about +10° C.), typically more than 3 months, preferably more than 6 months (at +5° C.), without trans-4-tert-butyl cyclohexanol crystallizing out of these compositions.

Such compositions comprising one or more (alkane) diols having 3 to 10 carbon atoms prepared according to the invention are readily further processable, in particular for (topical) cosmetic purposes.

The present invention als relates to the use of such a concentrated composition for the preparation of a cosmetic formulation or product or for the preparation of a medicament.

In another preferred embodiment of the present invention the one or more cosmetically acceptable carriers b) are selected from the group consisting of (i) one or more diols, preferably alkane diol(s), having 3 to 10 carbon atoms, preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, dipropylene glycol, preferably 1,2-butylene glycol, 1,2-pentanediol and/or dipropylene glycol, and/or (ii) a cosmetically acceptable carrier having a C log P value of at least 4, preferably of at least 5, more preferably of at least 6, and preferably selected from groups (ii-1) and/or (ii-2) and/or (ii-3) or mixtures thereof, said groups consisting of (ii-1) esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cet-earyl ethyl hexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, $C_{12-15}$-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or (ii-2) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or (ii-3) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methyl-phenyl siloxane, wherein, optionally and preferably, the weight ratio as described above of trans-4-tert-butyl cyclohexanol to cis-4-tert-butyl cyclohexanol, if present, is 75:25 or greater, preferably greater than 80:20, more preferably greater than 90:10, most preferably greater than 95:5.

The C log P value (also known as log Pow) is the decimal logarithm of the distribution coefficient of a substance or material between 1-octanol to water. C log P values are well known in the chemical arts as a calculated value that represents the relative affinity that a substance or material has for partitioning between octanol and water. C log P values can be obtained or calculated as described and referenced in WO 2008/114189.

Such preferred compositions or products comprising one or more cosmetically acceptable carriers b) according to the invention are easy to handle and stable over a long period of time, typically more than 3 months, preferably more than 6 months, without trans-4-tert-butyl cyclohexanol crystallizing out of these compositions, which is particularly of importance in (cosmetic) compositions or (cosmetic) products comprising water in an amount of 10 wt. % or more, based on the total weight of the formulation or product, or comprising a water and an oil phase, in particular emulsions, e.g. of the O/W— or W/O-type.

These compositions are readily further processable, in particular for (topical) cosmetic purposes.

Compositions and products according to the present invention advantageously comprise a total amount of 5 to 70 wt. %, preferably 7.5 to 60 wt. %, more preferably 10 to 50 wt. %, even more preferably 10-40 wt. %, of the one or more (preferred) cosmetically acceptable carriers b), in each case based on the total weight of the composition or product.

It was also found that compositions and products (in particular emulsions having a water content of more than 40 wt. %, based on the total weight of the emulsion) according to the present invention had improved storage stability (more than 3 months, generally more than 5 months) without trans-4-tert-butyl cyclohexanol (re-)crystallizing from these compositions and products when a total amount of 10 wt. % or more of the one or more (preferred) cosmetically acceptable carriers b) were present in case the amount of trans-4-tert-butyl cyclohexanol was about 0.25 wt. % to 0.5 wt. %, and a total amount of 15 wt. % or more (preferably up to 30 wt. %) of the one or more (preferred) cosmetically acceptable carriers b) were present in case the amount of trans-4-tert-butyl cyclohexanol was higher than 0.5 wt. % to about 1.0 wt. %, a total amount of 20 wt. % or more (preferably up to 35 wt. %) of the one or more (preferred) cosmetically acceptable carriers b) were present in case the amount of trans-4-tert-butyl cyclohexanol was higher than 1.0 wt. % to about 2.0 wt. %, in each case based on the total weight of the composition or product.

In some preferred embodiments compositions and products according to the present invention comprise water in an amount of up to 98 wt. %, preferably 10 to 95 wt. %, more preferably 25 to 90 wt. %, in each case based on the total weight of the composition or product.

In another preferred embodiment a composition or product according to the present invention additionally comprises one or more fragrance materials, preferably having a C log P value of at least 3, preferably of at least 4, more preferably of at least 5. Suitable fragrance materials are mentioned in S. Arctander, Perfume and Flavor Chemicals, Vol. I and II, Montclair, N.J., 1969, self-published or H. Surburg and J. Panten, Common Fragrance and Flavor Materials, 5th. Ed., Wiley-VCH, Weinheim 2006, particularly those explicitly mentioned in US 2008/0070825.

Compositions and products according to the present invention advantageously comprise a total amount of 0.1 to 5 wt. %, preferably 0.2 to 4 wt. %, more preferably 0.25 to 3 wt. %, even more preferably 0.3-2.5 wt. %, of the one or more (preferred) fragrance materials, in each case based on the total weight of the composition or product.

In a further preferred embodiment a composition or product according to the present invention additionally comprises one or more of fragrance materials having a boiling point of 250° C. or greater (at 1013 mbar). The total amount of fragrance materials having a boiling point of 250° C. or greater (at 1013 mbar) preferably is at least 10 wt. %, more preferably at least 20 wt. %, based on the total amount of fragrance materials present in a composition or product according to the present invention.

More preferably the fragrance materials, preferably having a boiling point of 250° C. or greater at 1013 mbar, are selected from (here in some cases the normal industrial product names and registered trademarks of various firms are given):

alpha-amyl cinnamic aldehyde, alpha-hexyl cinnamic aldehyde, 2-phenoxyethylisobutyrate (Phenirat), methyl dihydrojasmonate [preferably with a content of cis-isomers of >60 by weight (Hedione, Hedione HC)], 4,6,6,7,8,8-hexamethyl-1,3,4,6,7,8-hexahydrocyclopenta[g]benzopyran (Galaxolide), benzylsalicylate, 2-methyl-3-(4-tert-butylphenyl)propanal (Lilial), 4,7-methano-3a,4,5,6,7,7a-hexahydro-5-indenyl acetate and/or 4,7-methano-3a,4,5,6,7,7a-hexahydro-6-indenyl acetate (Herbaflorat), styrallyl acetate (1-phenylethyl acetate), octahydro-2,3,8,8-tetramethyl-2-acetonaphthone and/or 2-acetyl-1,2,3,4,6,7,8-octahydro-2,3,8, 8-tetramethylnaphthaline (Iso E Super), hexylsalicylate, 4-tert.-butylcyclohexyl acetate (Oryclon), 2-tert.-butylcyclohexyl acetate (Agrumex HC), alpha-ionone (4-(2,2,6-trimethyl-2-cyclohexen-1-yl)-3-buten-2-one), 4-(4-hydroxy-4-methylpentyl)-3-cyclohexene carboxaldehyde (Lyral), (E)- and/or (Z)-3-methylcyclopentadec-5-enone (Muscenone), 15-pentadec-11-enolide and/or 15-pentadec-12-enolide (Globalide), 15-cyclopentadecanolide (Macrolide), 1-(5,6,7, 8-tetrahydro-3,5,5,6,8,8-hexamethyl-2-naphthalenyl)ethanone (Tonalide), ethylene brassylate, 2-ethyl-4-(2,2,3-trimethyl-3-cyclopenten-1-yl)-2-buten-1-ol (Sandranol), alpha-Santalol, 2,2-dimethyl-3-(3-methylphenyl)-propanol (Majantol), allyl heptanoate, 4-methylacetophenone, (4aR, 5R,7aS,9R)-octahydro-2,2,5,8,8,9a-hexamethyl-4H-4a,9-methanoazuleno(5,6-d)-1,3-dioxol) (Ambrocenide), Timberol (1-(2,2,6-trimethylcyclohexyl)hexan-3-ol), benzylacetone, methyl cinnamate, 3a,6,6,9a-tetramethyldodecahydronaphtho[2,1-b]furan (Ambroxid).

The total amount of fragrance materials selected from the above group, preferably having a boiling point of 250° C. or greater at 1013 mbar, preferably is at least 10 wt. %, more preferably at least 20 wt. %, based on the total amount of fragrance materials present in a composition or product according to the present invention.

According to a further preferred embodiment a composition or product according to the present invention is—in contrast to WO 2008/117254—free of 2,6,10,10-Tetramethyl-1-oxaspiro[4.5]decan-6-ol (CAS number 65620-50-0).

Compositions according to the present invention advantageously additionally comprise one or more actives providing a benefit for the skin, in particular other skin irritation-reducing or skin-soothing agents, preferably selected from the group consisting of anti-inflammatory agents, physiological cooling agents, compounds that alleviate itching and/or compounds that alleviate reddening which are suitable for cosmetic and/or dermatological applications.

Also preferred composition according to the present invention comprise the one or more actives selected from the groups consisting of:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone; and/or
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone; and/or
(iii) natural or naturally occurring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or Echinacea, and/or
(iv) pure substances, preferably alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, glabridin and licochalcone A; and/or
(v) skin care agents, preferably skin moisture retention regulators or skin repair agents, preferably selected from the group consisting of sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts; and/or
(vi) physiological cooling agents, preferably selected from the group consisting of menthone glycerol acetal (also known as Frescolat®MGA), menthyl lactate (also known as Frescolat®ML, menthyl lactate is preferably l-menthyl lactate, in particular l-menthyl l-lactate), substituted menthyl-3-carboxylic acid amides (e.g. menthyl-3-carboxylic acid N-ethylamide, also known as WS-3, N$^\alpha$-(L-menthanecarbonyl)glycine ethyl ester, also known as WS-5), 2-isopropyl-N-2,3-trimethylbutanamide (also known as WS-23), substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin.

Preferably said compositions comprise one or more actives selected from the groups consisting of:
(iii) extracts or fractions from camomile, Aloe vera, oats, calendula, arnica, honeysuckle, rosemary, witch hazel, ginger or Echinacea; and/or
(iv) alpha-bisabolol, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, and licochalcone A; and/or
(v) urea, hyaluronic acid, allantoin, panthenol, lanolin, alpha-hydroxy acids (preferably citric acid, lactic acid), vitamin E and derivatives (preferably tocopherol, tocopheryl acetate).

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

The amount of other antiirritants (one or more compounds, other than trans-4-tert-butyl cyclohexanol) in the formulation of the present invention is preferably 0.0001 to 20 wt. %, particularly preferably 0.0001-10 wt. %, in particular 0.001-5 wt. %, based on the total weight of the formulation.

The formulation according to the invention or the liquid or solid formulation comprising the formulation can furthermore also be further processed by encapsulation. According to the invention, the formulation according to the invention and/or the liquid or solid formulation comprising this is encapsulated with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

The cosmetic, dermatological or therapeutic products according to the invention can be produced by conventional processes known per se, such that trans-4-tert-butyl cyclohexanol is incorporated into (topical) cosmetic, dermatological or therapeutic products which can have a conventional composition and which in addition to the aforementioned effects can also be used for the treatment, care and cleansing of the skin or hair.

Preferred fields of use for compositions according to the invention are (preferably topical) cosmetic, dermatological or therapeutic products which serve for cosmetic or dermatological light protection, for treatment, care and cleansing of the skin and/or hair or as a make-up product in decorative cosmetics. Such products can accordingly be present e.g. as a cleansing composition, such as e.g. soap, syndet, liquid washing, shower and bath preparation, skin care composition, such as e.g. emulsion (as a solution, dispersion, suspension; cream, lotion or milk of the W/O, O/W or multiple emulsion, PIT emulsion, emulsion foam, micro- or nanoemulsion, Pickering emulsion type, depending on the preparation process and constituents), ointment, paste, gel (including hydro-, hydrodispersion-, oleogel), alcoholic or aqueous/alcoholic solution, oil, toner, balsam, serum, powder (e.g. face powder, body powder), soaking liquid for wipes, Eau de Toilette, Eau de Cologne, perfume, wax, including the presentation form as a mask, mousse, stick, pencil, roll-on, (pump) spray, aerosol (foaming, non-foaming or after-foaming), skin care composition (as described above) as a foot care composition (including keratolytics, deodorant), as an insect repellent composition, as a sunscreen composition, as a self-tanning composition and/or aftersun preparation, skin care composition as a shaving composition or after-shave, as a hair-removing composition, as a hair care composition, such as e.g. shampoo (including shampoo for normal hair, for greasy hair, for dry, stressed (damaged) hair, 2-in-1 shampoo, anti-dandruff shampoo, baby shampoo, shampoo for a dry scalp, shampoo concentrate), conditioner, hair treatment cure, hair tonic, hair lotion, hair rinse, styling cream, pomade, permanent wave and fixing compositions, hair smoothing composition (straightening composition, relaxer), hair setting composition, styling aid (e.g. gel or wax); blonding composition, hair colouring composition, such as e.g. temporary, directly absorbed, semi-permanent hair colouring composition, permanent hair colouring composition), skin care composition as a decorative body care composition, such as e.g. nail care composition (nail varnish and nail varnish remover), decorative cosmetic (e.g. powder, eye shadow, kajal pencil, lipstick, mascara), make-up, make-up remover, skin care composition as a deodorant and/or antiperspirant.

Preferred products according to the present inventions are selected from the group of cosmetic products for treatment, protecting, care and cleansing of the skin and/or hair or as a make-up product, preferably as a leave-on product (meaning that trans-4-tert-butyl cyclohexanol stays on the skin for a longer period of time, e.g. compared to rinse-off products, so that the skin-irritation reducing action thereof is more pronounced), more preferably in the form or selected from the product group consisting of alcoholic or aqueous/alcoholic solution, dispersion, suspension, emulsion (preferably cream, lotion or milk of the W/O, O/W or multiple emulsion, PIT emulsion, emulsion foam, micro-, nanoemulsion, Pickering emulsion type), ointment, paste, gel (preferably hydro-, hydrodispersion-, oleogel), balm, serum, powder, wipe, Eau de Toilette, Eau de Cologne, perfume, stick, roll-on, (pump) spray, aerosol, leave-on skin care composition (preferably face-care composition), leave-on insect repellent composition, sunscreen composition, skin-lightening composition, self-tanning composition, aftersun preparation, after-shave composition, hair care composition, preferably conditioner, hair lotion, hair tonic, styling cream, pomade, styling aid (preferably gel or wax), decorative cosmetic composition (preferably face powder, eye shadow, kajal pencil, lipstick), deodorant and/or antiperspirant composition.

The present invention also relates to a cosmetic or therapeutic method for prophylaxis of and/or treatment of human skin irritation, comprising the step of
provision of trans-4-tert-butyl cyclohexanol or a cosmetically or pharmaceutically acceptable salt thereof, in particular the $Na^+$, $K^+$, $NH_4^+$, $Mg^{2+}$ or $Ca^{3+}$ salt, or of a composition or a medicament (pharmaceutical composition) according to the present invention,
application of trans-4-tert-butyl cyclohexanol, of the composition or of the medicament to non-irritated (prophylaxis) or irritated (treatment) skin in an effective amount, said application preferably remaining for at least 5 minutes, more preferably for at least 10 minutes, on said skin ("leave-on product").

Compositions and products, in particular (topical) cosmetic products, according to the present invention can advantageously comprise (apart from trans-4-tert-butyl cyclohexanol used according to the invention) suitable auxiliary substances and additives, such as, for example:

preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, anti-cellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

The (in particular topical) cosmetic or pharmaceutical products according to the invention can comprise cosmetic auxiliary substances and additives such as are conventionally used in such formulations, e.g. sunscreen agents, preservatives, bactericides, fungicides, virucides, cooling active compounds, insect repellents (e.g. DEET, IR 3225), plant extracts, plant parts, antiinflammatory active compounds, substances which accelerate wound healing (e.g. chitin or chitosan and derivatives thereof), film-forming substances (e.g. polyvinylpyrrolidones or chitosan or derivatives thereof), antioxidants, vitamins, 2-hydroxycarboxylic acids (e.g. citric acid, malic acid, L-, D- or dl-lactic acid), skin-colouring agents (e.g. walnut extracts or dihydroxyacetone), active compounds for promoting hair growth or inhibiting hair growth, skin care compositions (e.g. cholesterol, ceramides, pseudoceramides), softening, moisturizing and/or humectant substances, fats, oils, saturated fatty acids, mono- or polyunsaturated fatty acids, α-hydroxy acids, polyhydroxy-fatty acids or derivatives thereof, waxes or other conventional constituents of a cosmetic or dermatological formulation, such as alcohols, polyols, polymers, foam stabilizers, electrolytes, organic solvents, silicone derivatives of chelating agents (e.g. ethylenediaminetetraacetic acid and derivatives), antidandruff active compounds (e.g. climbazole, ketoconazole, piroctonoleamine, zinc pyrithione), hair care agents, perfumes, substances for preventing foaming, dyestuffs, pigments which have a colouring action, thickening agents (advantageously silicon dioxide, aluminium silicates, such as e.g. bentonites, polysaccharides or derivatives thereof, e.g. hyaluronic acid, guar bean flour, xanthan gum, hydroxypropylmethylcellulose or allulose derivatives, particularly advantageously polyacrylates, such as e.g. Carbopols or polyurethanes), surface-active substances and emulsifiers.

Auxiliary substances and additives (excluding water) can generally be included in products according to the present invention in quantities of 1 to 95 wt. %, preferably 5 to 70 wt. %, more preferably 5 to 50 wt. %, in each case based on the total weight of the product. The amounts of cosmetic or dermatological auxiliary agents and additives and perfume to be used in each case can easily be determined by the person skilled in the art by simple trials, depending on the nature of the particular product.

The products according to the present invention preferably contain water in a quantity of up to 98 wt. %, preferably 10 to 95 wt. %, more preferably 25 to 90 wt. %, even more preferably 40 to 90 wt. %, in each case based on the total weight of the product.

The formulations according to the invention can also comprise antioxidants, it being possible for all the antioxidants which are suitable or usual for cosmetic and/or dermatological uses to be used. The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), (metal) chelators, e.g. α-hydroxy-fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glycosides, such as e.g. 6-O-acyl-2-O-α-D-glucopyranosyl-L-ascorbic acid, 6-O-acyl-2-O-β-D-glucopyranosyl-L-ascorbic acid, 2-O-α-D-glucopyranosyl-L-ascorbic acid or 2-O-β-D-glucopyranosyl-L-ascorbic acid), tocopherols and derivatives thereof (e.g. vitamin E acetate), vitamin A and derivatives thereof (vitamin A palmitate) as well as coniferylbenzoate of benzoin resin, rutic acid and derivatives thereof, α-glucosylrutin, quercetin and derivatives thereof, rosemary acid, carnosol, carnosol acid, resveratrol, caffeic acid and derivatives thereof, sinapic acid and derivatives thereof, ferulic acid and derivatives thereof, furfurylideneglucitol, curcuminoids, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and derivatives (salts, esters, ethers, sugars, nucleotides, nucleosides, peptides and lipids) of these active compounds mentioned or antioxidatively active extracts or fractions from plants, such as e.g. green tea, rooibos, honeybush, grape, rosemary, sage, Melissa, thyme, lavender, olive, oats, cocoa, ginkgo, ginseng, liquorice, honeysuckle, Sophora, Pueraria, *Pinus*, Citrus, *Phyllanthus emblica* or St. John's wort.

The amount of antioxidants (one or more compounds) in the formulations according to the invention is preferably 0.01 to 20 wt. %, particularly preferably 0.05 to 10 wt. %, in particular 0.2-5 wt. %, based on the total weight of the formulation.

The formulations and products according to the present invention can also comprise physiological warming (heating) agents, which in some cases are TRPV1 agonists and thus are substances which may cause skin irritations. Such physiological warming agents preferably are selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, zingerone, capsaicin, dihydrocapsaicin, nordihydrocapsaicin, homocapsaicin, homodihydrocapsaicin, iso-propyl alcohol, iso-amylalcohol, benzyl alcohol, eugenol, cinnamon oil, cinnamic aldehyde, and mixtures thereof. The formulations according to the invention advantageously comprise at least one UVA filter and/or at least one UVB filter and/or at least one inorganic pigment. In this context, the formulations can be in various forms such as are conventionally employed e.g. for sunscreen formulations for protecting the skin and hair against ultraviolet radiation. They can thus form e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol. In this context, the total amount of UV-filter substances is from 0.01 wt. % to 40 wt. %, preferably 0.1 to 10 wt. %, in particular 1.0 to 5.0 wt. %, based on the total weight of the formulations.

Advantageous UV filters are e.g.: p-aminobenzoic acid, p-aminobenzoic acid ethyl ester (25 mol) ethoxylated, p-dimethylaminobenzoic acid 2-ethylhexyl ester, p-aminobenzoic acid ethyl ester (2 mol) N-propoxylated, p-aminobenzoic acid glycerol ester, salicylic acid homomethyl ester (homosalate) (Neo Heliopan®HMS), salicylic acid 2-ethylhexyl ester (Neo Heliopan®OS), triethanolamine salicylate, 4-isopropylbenzyl salicylate, anthranilic acid menthyl ester (Neo Heliopan®MA), diisopropylcinnamic acid ethyl ester, p-methoxycinnamic acid 2-ethylhexyl ester (Neo Heliopan®AV), diisopropylcinnamic acid methyl ester, p-methoxycinnamic acid isoamyl ester (Neo Heliopan®E 1000), p-methoxycinnamic acid diethanolamine salt, p-methoxycinnamic acid isopropyl ester, 2-ethylhexyl 2-cyano-3,3-diphenylacrylate (Neo Heliopan®303), ethyl 2-cyano-3,3'-diphenylacrylate, 2-phenylbenzimidazolesulfonic acid and salts (Neo Heliopan®Hydro), 3-(4'-trimethylammonium)-benzylidene-bornan-2-one methyl-sulfate, terephthalylidene-dibornanesulfonic acid and salts (Mexoryl®SX), 4-t-butyl-4'-methoxy-dibenzoylmethane (avobenzone)/(Neo Heliopan®357), β-Imidazole-4(5)-acrylic acid (urocanic acid), 2-hydroxy-4-methoxybenzophenone (Neo Heliopan®BB), 2-hydroxy-4-methoxybenzophenone-5-sulfonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, 3-(4'-sulfo)benzylidene-bornan-2-one and salts, 3-(4'-methylbenzylidene)-d,l-camphor (Neo Heliopan®MBC), 3-benzylidene-d,l-camphor, 4-isopropyldibenzoylmethane, 2,4,6-trianilino-(p-carbo-2'-ethylhexyl-1'-oxy)-1,3,5-triazine, phenylene-bis-benzimidazyl-tetrasulfonic acid disodium salt (Neo Heliopan®AP), 2,2'-(1,4-phenylene)-bis-(1H-benzimidazole-4,6-disulfonic acid), monosodium salt, N-[(2 and 4)-[2-(oxoborn-3-ylidene)methyl]benzyl]-acrylamide polymer, phenol, -(2H-benzotriazol-2-yl)-4-methyl-6-(2-methyl-3(1,3,3,3-tetramethyl-1-(trimethylsilyl)-oxy)-disiloxyanyl)-propyl), (Mexoryl®XL), 4,4'-[(6-[4-(1,1-dimethyl)-aminocarbonyl)-phenylamino]-1,3,5-triazine-2,4-diyl)diimino]-bis-(benzoic acid 2-ethylhexyl ester) (Uvasorb®HEB), 2,2'-methylene-bis-(6-(2H-benzotriazol-2-yl)-4-(1,1,3,3-tetramethylbutyl)-phenol), (Tinosorb®M), 2,4-bis-[4-(2-ethylhexyloxy)-2-hydroxyphenyl]-1,3,5-triazine, benzylidene malonate-polysiloxane (Parsol®SLX), glyceryl ethylhexanoate dimethoxycinnamate, disodium 2,2'-dihydroxy-4,4'-dimethoxy-5,5'-disulfo-benzophenone, dipropylene glycol salicylate, sodium hydroxymethoxybenzophenone-sulfonate, 4,4',4-(1,3,5-triazine-2,4,6-triyltriimino)-tris-benzoic acid tris(2-ethylhexyl ester) (Uvinul®T150), 2,4-bis-[{(4-(2-ethyl-hexyloxy)-2-hydroxy}-phenyl]-6-(4-methoxyphenyl)-1,3,5-triazine, (Tinosorb®S), 2,4-bis-[{(4-(3-sulfonato)-2-hydroxy-propyloxy)-2-hydroxy}-phenyl]-6-(4-methoxyphenyl)-1,3,5-triazine sodium salt, 2,4-bis-[{(3-(2-propyloxy)-2-hydroxy-propyloxy)-2-hydroxy}-phenyl]-6-(4-methoxy-phenyl)-1,3,5-triazine, 2,4-bis-[{4-(2-ethyl-hexyloxy)-2-hydroxy}-phenyl]-6-[4-(2-methoxyethyl-carbonyl)-phenylamino]-1,3,5-triazine, 2,4-bis-[{4-(3-(2-propyloxy)-2-hydroxy-propyloxy)-2-hydroxy}-phenyl]-6-[4-(2-ethylcarboxyl)-phenylamino-]1,3,5-triazine, 2,4-bis-[{4-(2-ethyl-hexyloxy)-2-hydroxy}-phenyl]-6-(1-methyl-pyrrol-2-yl)-1,3,5-triazine, 2,4-bis-[{4-tris-(trimethylsiloxy-silylpropyloxy)-2-hydroxy}-phenyl]-6-(4-methoxyphenyl)-1,3,5-triazine, 2,4-bis-[{4-(2"-methylpropenyloxy)-2-hydroxy}-phenyl]-6-(4-methoxyphenyl)-1,3,5-triazine, 2,4-bis-[{4-(1',1',1',3',5',5',5'-heptamethylsiloxy-2"-methyl-propyloxy)-2-hydroxy}-phenyl]-6-(4-methoxyphenyl)-1,3,5-triazine, 2-(4-diethylamino-2-hydroxybenzoyl)-benzoic acid hexyl ester (Uvinul® A Plus) and indanylidene compounds according to DE 100 55 940 (=WO 02/38537).

In this context, UV absorbers which are particularly suitable for combination are p-aminobenzoic acid, 3-(4'-trimethylammonium)-benzylidene-bornan-2-one methyl-sulfate, salicylic acid homomethyl ester (Neo Heliopan®HMS), 2-hydroxy-4-methoxy-benzophenone (Neo Heliopan®BB), 2-phenylbenzimidazolesulfonic acid (Neo Heliopan®Hydro), terephthalylidene-dibornanesulfonic acid and salts (Mexoryl®SX), 4-tert-butyl-4'-methoxydibenzoylmethane (Neo Heliopan®357), 3-(4'-sulfo)benzylidene-bornan-2-one and salts, 2-ethylhexyl 2-cyano-3,3-diphenylacrylate (Neo Heliopan®303), N-[(2 and 4)-[2-(oxoborn-3-ylidene)methyl]benzyl]-acrylamide polymer, p-methoxycinnamic acid 2-ethylhexyl ester (Neo Heliopan®AV), p-aminobenzoic acid ethyl ester (25 mol) ethoxylated, p-methoxycinnamic acid isoamyl ester (Neo Heliopan®E1000), 2,4,6-trianilino-(p-carbo-2'-ethylhexyl-1'-oxy)-1,3,5-triazine (Uvinul®T150), phenol, 2-(2H-benzotriazol-2-yl)-4-methyl-6-(2-methyl-3(1,3,3,3-tetramethyl-1-(trimethylsilyl)-oxy)-disiloxyanyl)-propyl), (Mexoryl®XL), 4,4'4[(6-[4-(1,1-dimethyl)-aminocarbonyl)-phenylamino-]1,3,5-triazine-2,4-diyl)-diimino]-bis-(benzoic acid 2-ethylhexyl ester), (UvasorbHEB), 3-(4'-methylbenzylidene)-d,l-camphor (Neo Heliopan®MBC), 3-benzylidenecamphor, salicylic acid 2-ethylhexyl ester (Neo Heliopan®OS), 4-dimethylaminobenzoic acid 2-ethylhexyl ester (Padimate O), hydroxy-4-methoxy-benzophenone-5-sulfonic acid and Na salt, 2,2'-methylene-bis-(6-(2H-benzotriazol-2-yl)-4-(1,1,3,3-tetramethylbutyl)-phenol), (Tinosorb®M), phenylene-bis-benzimidazyl-tetrasulfonic acid disodium salt (Neo Heliopan®AP), 2,4-bis-[{(4-(2-ethyl-hexyloxy)-2-hydroxy}-phenyl]-6-(4-methoxyphenyl)-1,3,5-triazine, (Tinosorb®S), benzylidene malonate-polysiloxane (Parsol®SLX), menthyl anthranilate (Neo Heliopan®MA), 2-(4-diethylamino-2-hydroxybenzoyl)-benzoic acid hexyl ester (Uvinul® A Plus) and indanylidene compounds according to DE 100 55 940 (=WO 02/38537).

Advantageous inorganic sunscreen pigments are finely disperse metal oxides and metal salts, for example titanium dioxides, zinc oxide (ZnO), iron oxides (e.g. $Fe_2O_3$), aluminium oxide ($Al_2O_3$); cerium oxides (e.g. $Ce_2O_3$), manganese oxides (e.g. MnO), zirconium oxide ($ZrO_2$), silicon oxide ($SiO_2$), mixed oxides of the corresponding metals and mixtures of such oxides, barium sulfate and zinc stearate. They are particularly preferably pigments based on $TiO_2$ or zinc oxide. In preferred embodiments, the particles have an average diameter of less than 100 nm, preferably between 5 and 50 nm and particularly preferably between 15 and 30 nm. They can have a spherical shape, but those particles which have an ellipsoid shape or a shape which deviates otherwise from the spherical can also be employed. The pigments can also be in a form treated on the surface, i.e. hydrophilized or hydrophobized. Typical examples are coated titanium dioxides, such as e.g. titanium dioxide T 805 (Degussa) or Eusolex® Eusolex®T2000 (Merck), or coated zinc oxide, such as e.g. Zinc Oxide NDM. In this context, possible hydrophobic coating agents are, above all, silicones, and in this case specifically trialkoxyoctysilanes or simethicone. So-called micro- or nanopigments are preferably employed in sunscreen compositions. Zinc micro- or nanopigments are preferably employed.

The total amount of inorganic pigments, in particular hydrophobic inorganic micropigments, in the finished cosmetic or dermatological formulations is advantageously in the range of from 0.1 to 30 wt. %, preferably 0.1 to 10.0, in particular 0.5 to 6.0 wt. %, based on the total weight of the formulations.

Cosmetic formulations according to the invention which comprise a formulation according to the invention having a skin irritation-reducing action can also comprise active compounds and active compound combinations against ageing of the skin and wrinkles. According to the invention, all the active compounds against ageing of the skin and wrinkles which are suitable or usual for cosmetic and/or dermatological uses can be used here. Advantageous active compounds against ageing of the skin and wrinkles in this respect are soya protein or protein hydrolysates, soya isoflavones, hydrolyzed rice protein, hydrolysed hazelnut protein, oligopeptides from hydrolysed Hibiscus esculentus extract, wheat protein, β-glucans, e.g. from oats, and derivatives thereof, glycoproteins, ursolic acid and its salts, betulin, betulic acid and its salts, retinol, retinol palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, creatine or other synthetic or natural active compounds against ageing of the skin and wrinkles, it being possible for the latter also to be used in the form of an extract from plants, such as e.g. green tea, *Rubus fruticosus, Sanguisorba officinalis, Centella asiatica, Ribes nigrum, Passiflora incarnate, Filipendula ulmaria, Phyllanthus emblica, Potentilla* species, okra, algae, evening primrose, pomegranate, lady's mantle, rosemary, sage, Echinacea, birch, apple or soya.

Substances which are particularly preferred for use as further active compounds against ageing of the skin are β-glucans, and 1,3-1,4-linked β-glucan from oats, *Rubus fruticosus* extract or wheat protein is particularly preferred.

The formulations according to the invention can also comprise active compounds which stimulate shading or tanning of the skin and hair in a chemical or natural manner. A faster action based on synergistic effects is thereby achieved. Substances which are particularly preferred in this context are substrates or substrate analogues of tyrosinase, such as L-tyrosine, L-DOPA or L-dihydroxyphenylalanine, stimulators of tyrosinase activity or expression, such as theophylline, caffeine, propiomelanocortin peptides, such as ACTH, alpha-MSH, peptide analogues thereof and other substances which bind to the melanocortin receptor, peptides, such as Val-Gly-Val-Ala-Pro-Gly, Lys-Ile-Gly-Arg-Lys or Leu-Ile-Gly-Lys, purines, pyrimidines, folic acid, copper salts, such as copper gluconate, chloride or pyrrolidonate, flavonoids, flavanone glycosides, such as naringin and hesperidin, melanin derivatives, such as Melasyn-100 and MelanZe, diacylglycerols, aliphatic or cyclic diols, psoralene, prostaglandins and analogues thereof, activators of adenylate cyclase and compounds which activate the transfer of melanosomes into keratinocytes, such as serine proteases or agonists of the PAR-2 receptor, extracts from plants and plant parts of the *Chrysanthemum* species or *Sanguisorba* species, walnut extracts, urucum extracts, rhubarb extracts, erytrulose and dihydroxyacetone.

The formulations according to the invention can also be employed in combination with skin-lightening active compounds. According to the invention, all the skin-lightening active compounds which are suitable or usual for cosmetic and/or dermatological uses can be used here. Advantageous skin-lightening active compounds in this respect are kojic acid (5-hydroxy-2-hydroxymethyl-4-pyranone), kojic acid derivatives, such as e.g. kojic acid dipalmitate, arbutin, ascorbic acid, ascorbic acid derivatives, hydroquinone, hydroquinone derivatives, resorcinol, sulfur-containing molecules, such as e.g. cysteine, alpha-hydroxy acids (e.g. citric acid, lactic acid, malic acid) and derivatives thereof, N-acetyltyrosine and derivatives, undecenoylphenylalanine, gluconic acid, 4-alkylresorcinols, 4-(1-phenylethyl)-1,3-benzenediol, chromone derivatives, such as aloesin, flavonoids, thymol derivatives, 1-aminoethylphosphinic acid, thiourea derivatives, ellagic acid, nicotinamide, zinc salts, such as e.g. zinc chloride or gluconate, thujaplicin and derivatives, triterpenes, such as maslic acid, sterols, such as ergosterol, benzofuranones, such as senkyunolide, vinyl- and ethylguaiacol, inhibitors of nitrogen oxide synthesis, such as e.g. L-nitroarginine and derivatives thereof, 2,7-dinitroindazole or thiocitrullin, metal chelators (e.g. α-hydroxy-fatty acids, palmitic acid, phytic acid, lactoferrin, humic acid, bile acid, bile extracts, bilirubin, biliverdin, EDTA, EGTA and derivatives thereof), retinoids, soya milk, serine protease inhibitors or liponic acid or other synthetic or natural active compounds for lightening of the skin and hair, the latter also being used in the form of an extract from plants, such as e.g. bearberry extract, rice extract, liquorice root extract or constituents concentrated therefrom, such as glabridin or licochalcone A, Artocarpus extract, extract from *Rumex* and *Ramulus* species, extracts from pine species (*Pinus*) and extracts from *Vitis* species or stilbene derivatives concentrated therefrom, and extract from Saxifraga, mulberry, *Scutelleria* or/and grape.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate ($Zn(Gly)_2$), manganese(II) bicarbonate complexes ("pseudocatalases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, trehalose, erythrulose and dihydroxyacetone. Flavonoids which bring about skin and hair tinting or tanning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Formulations according to the invention can advantageously also comprise moisture retention regulators. The following substances e.g. are used as moisture retention regulators ("moisturizers"): sodium lactate, urea and derivatives, alcohols, glycerol, diols, such as propylene glycol, 1,2-pentanediol, 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulfate, lanolin, lanolin esters, amino acids, alpha-hydroxy acids (e.g. citric acid, lactic acid, malic acid) and derivatives thereof, mono-, di- and oligosaccharides, such as, for example, glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts.

Formulations according to the invention can also be employed together with osmolytes. Osmolytes which may be mentioned by way of example are: substances from the group consisting of sugar alcohols (myo-inositol, mannitol, sorbitol), quaternary amines, such as taurine, choline, betaine, betaine-glycine and ectoin, diglycerol phosphate, phosphorylcholine, glycerophosphorylcholines, amino acids, such as glutamine, glycine, alanine, glutamate, aspartate or proline, phosphatidylcholine, phosphatidylinositol and inorganic phosphates, as well as polymers of the compounds mentioned, such as proteins, peptides, poly-amino acids and polyols. All osmolytes at the same time have a skin-moisturizing action.

Formulations according to the invention can advantageously also comprise vitamins and vitamin precursors, it being possible for all the vitamins and vitamin precursors which are suitable or usual for cosmetic and/or dermatological uses to be used. Vitamins and vitamin precursors which may be mentioned by way of example are: vitamin A (retinol) and its derivatives (e.g. vitamin A acetate, vitamin A acid, vitamin A aldehyde, vitamin A palmitate, vitamin A propionate), vitamin B1 (thiamine) and its salts (e.g. vitamin B1 hydrochloride, vitamin B1 mononitrate, thiamine diphosphate, thiamine pyrophosphate), vitamin B12 (cobalamin), vitamin B2 (vitamin G, riboflavin) and its derivatives (e.g. vitamin B2 tetraacetate), vitamin B3 and its derivatives (e.g. nicotinamide ascorbate, nicotinamide glycollate, nicotinamide hydroxycitrate, nicotinamide lactate, nicotinamide malate, nicotinamide mandelate, nicotinamide salicylate, nicotinamide thioctate), vitamin B4 (adenine) and its derivatives (e.g. adenine riboside, disodium flavin adenine dinucleotide, nicotinamide adenine dinucleotide), provitamin B5, vitamin B5 (pantothenic acid) and its derivatives (e.g. acetyl pantothenyl ethyl ether, allantoin calcium pantothenate, allantoin DL-pantothenyl alcohol, bis(pantothenamidoethyl) disulfide, calcium pantothenate, hydroxyethyl pantothenamide MEA, sodium pantothenate, N-D-pantothenoyl-2-(2-aminoethoxy)ethanol, N-D-pantothenoyl-2-aminoethanol, N-hydroxyethoxyethyl pantothenamide, N-hydroxyethyl pantothenamide, pantothenamide MEA, pantothenol, pantothenic acid lactone, pantothenic acid polypeptide, pantothenyl ethyl ether), vitamin B6 (pyridoxol, pyroxidal, pyridoxamine) and its derivatives (e.g. pyridoxine dicaprylate, vitamin B6 dilaurate, vitamin B6 dioctanoate, vitamin B6 dipalmitate, pyridoxine glycyrrhetinate, vitamin B6 hydrochloride, vitamin B6 phosphate, vitamin B6 serine, vitamin B6 tripalmitate), vitamin C (ascorbic acid) and its derivatives (e.g. 3-O-ethyl ascorbic acid, allantoin ascorbate, aminopropyl ascorbyl phosphate, araboascorbic acid, monosodium salt, ascorbic acid palmitate, ascorbic acid polypeptide, ascorbosilane C, ascorbyl dipalmitate, ascorbyl glucoside, ascorbyl inositol nicotinate, ascorbyl linoleate, ascorbyl methylsilanol pectinate, ascorbyl nicotinamide, ascorbyl phosphate magnesium, ascorbyl stearate, ascorbyl tetraisopalmitate, ascorbyl tocopheryl maleate, calcium ascorbate, chitosan ascorbate, D-arabino-ascorbic acid, disodium ascorbyl sulfate, glucosamine ascorbate, inositol hexanicotinate hexa-ascorbate, isoascorbic acid, L-ascorbic acid, 2-(dihydrogen phosphate), trisodium salt, L-ascorbic acid, 2-[(3-cholest-5-en-3-yl hydrogen phosphate], monosodium salt, L-ascorbic acid, 2-O-D-glucopyranosyl-, L-ascorbic acid, 3-O-ethyl ether, magnesium ascorbate, magnesium ascorbylborate, methoxy PEG-7 ascorbic acid, methylsilanol ascorbate, potassium ascorbyl tocopheryl phosphate, potassium ascorbylborate, sodium ascorbate, sodium ascorbyl phosphate, sodium ascorbyl/cholesteryl phosphate, sodium isoascorbate, sodium L-ascorbyl 2-phosphate, tetrahexyldecyl ascorbate), provitamin D, vitamin D (calciol) and its derivatives (e.g. vitamin D2, vitamin D3), vitamin E (D-alpha-tocopherol) and its derivatives (e.g. di-alpha-tocopherol, polyoxypropylene/polyoxyethylene/tocopherol ether, polypropylene glycol/tocopherol ether, tocopherol cysteamine, tocopherol phosphate, sodium vitamin E phosphate, vitamin E acetate, vitamin E linoleate, vitamin E nicotinate, vitamin E succinate), vitamin F (essential fatty acids, linolenic acid and linoleic acid) and its derivatives (e.g. vitamin F ethyl ester, vitamin F glyceryl ester), vitamin H (vitamin B7, biotin), vitamin K1 (phylloquinone, phytonadione) and vitamin K3 (menadione, menaquinone).

Formulations according to the invention can likewise comprise one or more further plant extracts, which are conventionally prepared by extraction of the whole plant, but in individual cases also exclusively from blossom and/or leaves, wood, bark or roots of the plant. In respect of the plant extracts which can be used, reference is made in particular to the extracts which are listed in the table starting on page 44 of the 3rd edition of the Leitfaden zur Inhaltsstoffdeklaration kosmetischer Mittel [Manual of Declaration of the Constituents of Cosmetic Compositions], published by Industrieverband Körperpflegemittel and Waschmittel e.V. (IKW), Frankfurt. Extracts which are advantageous in particular are those from aloe, algae, apple, apricot, arnica, avocado, pear, stinging nettle, blackberry, calendula, ivy, hibiscus, oak bark, strawberry, spruce, honeysuckle, barley, ginkgo, ginseng, pomegranate, grapefruit, cucumber, oats, witch hazel, restharrow, henna, raspberry, elder, honeybush, hops, coltsfoot, kiwi, burdock, coconut, lavender, lime, linden, mallow, almond, mango, box holly, Melissa, olive, orange, peppermint, Pueraria, wild thyme, rooibos, rose, rosemary, horse chestnut, sage, sandalwood, yarrow, horsetail, Sophora, liquorice, dead nettle, tea (green, white, black), thyme, grape, juniper, willow, rose-bay willow-herb, hawthorn, wheat, lady's smock, cinnamon, lemon and lemongrass. In this context, the extracts from aloe vera, algae, arnica, stinging nettle, calendula, witch hazel, linden, ginseng, cucumber, rosemary and sage are particularly preferred. Mixtures of two or more plant extracts can also be employed. Extraction agents which can be used for the preparation of the plant extracts mentioned are, inter alia, water, alcohols and mixtures thereof. In this context, among the alcohols lower alcohols, such as ethanol and isopropanol, and also polyhydric alcohols, such as ethylene glycol, propylene glycol and butylene glycol, are preferred, and in particular both as the sole extraction agent and in mixtures with water. The plant extracts can be employed both in the pure and in the diluted form.

The formulations according to the invention moreover can also preferably comprise perspiration-inhibiting active compounds (antiperspirants) and odour absorbers. Perspiration-inhibiting active compounds which are employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning. Alongside aluminium salts, further substances are also possible, such as, for example, a) protein-precipitating substances, such as, inter alia, formaldehyde, glutaraldehyde, natural and synthetic tannins and trichloroacetic acid, which bring about blockage of the sweat glands on the surface, b) local anaesthetics (inter alia dilute solutions of e.g. lidocaine, prilocalne or mixtures of such substances), which eliminate sympathetic supply of the sweat glands by blockade of the peripheral nerve pathways, c) zeolites of the X, A or Y type, which, alongside the reduction in secretion of perspiration, also function as adsorbents for bad odours, and d) botulinus toxin (toxin of the bacterium *Chlostridium botulinum*), which is also employed in cases of hyperhidrosis, a pathologically increased secretion of perspiration, and the action of which is based on an irreversible blocking of the release of the transmitter substance acetylcholine, which is relevant for secretion of perspiration.

Odour absorbers are, for example, the laminar silicates described in DE 40 09 347, and of these in particular montmorillonite, kaolinite, nontronite, saponite, hectorite, bentonite and smectite, and furthermore, for example, zinc salts of ricinoleic acid. These likewise include deodorants, bactericidal or bacteriostatic deodorizing substances, such as e.g. hexachlorophene, 2,4,4'-trichloro-2' hydroxydiphenyl ether (Irgasan), 1,6-di-(4-chlorophenylbiguanido)-hexane (chlorhexidine) and 3,4,4'-trichlorocarbanilide, as well as the active agents described in DE 37 40 186, DE 39 38 140, DE 42 04 321, DE 42 29 707, DE 42 29 737, DE 42 37 081, DE 43 09 372 and DE 43 24 219, and cationic substances, such as e.g. quaternary ammonium salts, and odour absorbers, such as e.g. ®Grillocin (combination of zinc ricinoleate and various additives) or triethyl citrate, optionally in combination with ion exchange resins.

In various cases it may also be advantageous to employ formulations according to the invention in combination with substances which are chiefly employed for inhibition of the growth of undesirable microorganisms. In this respect, alongside conventional preservatives, further active compounds which are worth mentioning, alongside the large group of conventional antibiotics, are, in particular, the products relevant for cosmetics, such as triclosan, climbazole, zinc pyrithione, ichthyol, Octopirox (1-hydroxy-4-methyl-6-(2,4, 4-trimethylpentyl)-2(1H)-pyridone, 2-aminoethanol), chitosan, farnesol, octoxyglycerol, glycerol monolaurate, arylalkyl alcohols, such as e.g. phenylethyl alcohol, 3-phenyl-1-propanol, veticol or muguet alcohol, polyglycerol esters, such as e.g. polyglyceryl 3-caprylates, and aliphatic diols, such as e.g. 1,2-decanediol, or combinations of the substances mentioned, which are employed, inter alia, against underarm odour, foot odour or dandruff formation.

Formulations according to the invention can in numerous cases also advantageously comprise preservatives. Preservatives which are preferably chosen here are those such as benzoic acid and its esters and salts, 4-hydroxybenzoic acid and its esters (INCI: Parabens, preferably methylparaben, ethylparaben, butylparaben, propylparaben and/or isobutylparaben) and salts, propionic acid and its esters and salts, salicylic acid and its esters and salts, 2,4-hexadienoic acid (sorbic acid) and its esters and salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)-5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylenediguanide) hydrochloride, 2-phenoxyethanol, hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis-(hydroxy-methyl)-5,5-dimethyl-2,4-imidazolidinedione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$) trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidino-phenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate.

Cosmetic or dermatological formulations which comprise formulations according to the invention can also be in the form of emulsions.

The oily phase can advantageously be chosen from the following substance group:
mineral oils, mineral waxes
fatty oils, fats, waxes and other natural and synthetic fat substances, preferably esters of fatty acids with alcohols of low C number, e.g. with isopropanol, propylene glycol or glycerol, or esters of fatty alcohols with alkanoic acids of low C number or with fatty acids;
alkyl benzoates;
silicone oils, such as dimethylpolysiloxanes, diethylpolysiloxanes, diphenylpolysiloxanes and mixed forms thereof.

Compounds which can advantageously be employed are (a) esters of saturated and/or unsaturated branched and/or unbranched alkanecarboxylic acids having a chain length of from 3 to 30 C atoms and saturated and/or unsaturated, branched and/or unbranched alcohols having a chain length of from 3 to 30 C atoms, (b) esters of aromatic carboxylic acids and saturated and/or unsaturated, branched and/or unbranched alcohols having a chain length of from 3 to 30 C atoms. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oily phase can furthermore advantageously be chosen from the group consisting of branched and unbranched hydrocarbons and waxes, silicone oils and dialkyl ethers, the group consisting of saturated or unsaturated, branched or unbranched alcohols, and the fatty acid triglycerides, namely the triglycerol esters of saturated and/or unsaturated, branched and/or unbranched alkanecarboxylic acids having a chain length of from 8 to 24, in particular 12 to 18 C atoms. The fatty acid triglycerides can advantageously be chosen from the group consisting of synthetic, semi-synthetic and natural oils, e.g. olive oil, sunflower oil, soya oil, groundnut oil, rapeseed oil, almond oil, palm oil, coconut oil, palm kernel oil and more of the like. Any desired blends of such oil and wax components can also advantageously be employed. In some cases it is also advantageous to employ waxes, for example cetyl palmitate, as the sole lipid component of the oily phase, and the oily phase is advantageously chosen from the group which consists of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oily phase can furthermore have a content of cyclic or linear silicone oils or consist entirely of such oils, it being advantageous to use an additional content of other oily phase components in addition to the silicone oil or silicone oils. Cyclomethicone (e.g. decamethylcyclopentasiloxane) can advantageously be employed as a silicone oil.

However, other silicone oils, for example undecamethylcyclotrisiloxane, polydimethylsiloxane and poly(methylphenylsiloxane), can also advantageously be used. Mixtures of cyclomethicone and isotridecyl isononanoate and of cyclomethicone and 2-ethylhexyl isostearate are furthermore particularly advantageous.

Formulations in the form of an emulsion which comprise a formulation according to the invention advantageously comprise one or more emulsifiers. O/W emulsifiers can advantageously be chosen, for example, from the group consisting of polyethoxylated or polypropoxylated or polyethoxylated and polypropoxylated products.

According to the invention, the polyethoxylated or polypropoxylated or polyethoxylated and polypropoxylated O/W emulsifiers employed are particularly advantageously chosen from the group consisting of substances having HLB values of 11-18, very particularly advantageously having HLB values of 14.5-15.5, if the O/W emulsifiers contain saturated radicals R and R'. If the O/W emulsifiers contain unsaturated radicals R and/or R', or isoalkyl derivatives are present, the preferred HLB value of such emulsifiers can also be lower or higher.

It is of advantage to choose the fatty alcohol ethoxylates from the group consisting of ethoxylated stearyl alcohols, cetyl alcohols and cetyl stearyl alcohols (cetearyl alcohols).

Advantageous W/O emulsifiers which can be employed are: fatty alcohols having 8 to 30 carbon atoms, monoglycerol esters of saturated and/or unsaturated, branched and/or unbranched alkanecarboxylic acids having a chain length of from 8 to 24, in particular 12 to 18 C atoms, diglycerol esters of saturated and/or unsaturated, branched and/or unbranched alkanecarboxylic acids having a chain length of from 8 to 24, in particular 12 to 18 C atoms, monoglycerol ethers of saturated and/or unsaturated, branched and/or unbranched alcohols having a chain length of from 8 to 24, in particular 12 to 18 C atoms, diglycerol ethers of saturated and/or unsaturated, branched and/or unbranched alcohols having a chain length of from 8 to 24, in particular 12 to 18 C atoms, propylene glycol esters of saturated and/or unsaturated, branched and/or unbranched alkanecarboxylic acids having a chain length of from 8 to 24, in particular 12 to 18 C atoms and sorbitan esters of saturated and/or unsaturated, branched and/or unbranched alkanecarboxylic acids having a chain length of from 8 to 24, in particular 12 to 18 C atoms.

Formulations according to the invention for cosmetic (topical) prophylactic (preventive) treatment of the skin can regularly comprise a high content of care substances. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, oat oil, sperm oil, beef tallow, neat's foot oil and lard, and optionally further care constituents, such as, for example, fatty alcohols having 8-30 C atoms. The fatty alcohols here can be saturated or unsaturated and linear or branched. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and Guerbet alcohols thereof, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as e.g. beef tallow, groundnut oil, colza oil, cottonseed oil, soya oil, sunflower oil, palm kernel oil, linseed oil, maize oil, castor oil, rape oil, sesame oil, cacao butter and coconut fat, can furthermore be employed.

Care substances which can be combined in an outstanding manner with formulations according to the invention moreover also include waxes, such as e.g. candelilla wax or carnauba wax ceramides, where ceramides are understood as meaning N-acylsphingosins (fatty acid amides of sphingosin) or synthetic analogues of such lipids (so-called pseudoceramides), which significantly improve the water retention capacity of the stratum corneum.

phospholipids, for example soya lecithin, egg lecithin and cephalins vaseline, paraffin oils and silicone oils; the latter include, inter alia, dialkyl- and alkylarylsiloxanes, such as dimethylpolysiloxane and methylphenylpolysiloxane, as well as alkoxylated and quaternized derivatives thereof.

The invention also provides the use of a formulation according to the invention or of a medicament (pharmaceutical composition) according to the invention for prophylaxis (prevention) of skin irritations and/or for treatment of skin irritations for medical and/or other than medical purposes. It also relates to a medicament for the treatment of pain conditions. The invention likewise provides the use of a formulation according to the invention or of a medicament (pharmaceutical composition) according to the invention for the preparation of a medicament for treatment of skin irritations and/or pain.

The invention furthermore provides the use of a formulation according to the invention or of a medicament according to the invention for the preparation of a cosmetic or pharmaceutical formulation.

In some embodiments, in particular for medical purposes, it is advantageous to administer a composition according to the present invention orally e.g. in the form of (compressed) tablets, dragees, comprimates, powders, capsules, juices, solutions and granules or in form of orally consumable products used for alimentation which in addition to their function as foodstuff provide beauty from inside.

The invention also provides the use of a formulation according to the invention or of a medicament (pharmaceutical composition) according to the invention for reducing, eliminating or suppressing the skin-irritating action of a substance or substance mixture.

The present invention also relates to a medicament (pharmaceutical composition) for a human being, in particular for treatment of human skin irritation or for treating pain, comprising trans-4-tert-butyl cyclohexanol or a pharmaceutically acceptable salt thereof, in particular the $Na^+$, $K^+$, $NH_4^+$, $Mg^{2+}$ or $Ca^{2+}$ salt, in an effective amount, preferably in an amount in the range of 0.1 to 20 wt. %, preferably 0.5 to 10 wt. %, based on the total weight of the medicament.

The term "pharmaceutical composition" as used herein comprises trans-4-tert-butyl cyclohexanol of the present invention and one or more pharmaceutically acceptable carriers. As described above, trans-4-tert-butyl cyclohexanol can be formulated as pharmaceutically acceptable salt. Typical pharmaceutically acceptable salts include those salts prepared by reaction of trans-4-tert-butyl cyclohexanol of the present invention with a pharmaceutically acceptable inorganic base. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole.

The pharmaceutical compositions are, preferably, administered topically or systemically. Suitable routes of administration conventionally used for drug administration are oral, intravenous, dermal or parenteral administration as well as inhalation.

The pharmaceutical carrier must be acceptable in the sense of being compatible with the other ingredients of the formulation and being not deleterious to the recipient thereof. The pharmaceutical carrier employed shall be, preferably, a solid, a gel or a liquid. Preferred pharmaceutical solid carriers are lactose, terra alba, sucrose, talc, gelatin, agar, pectin, acacia, magnesium stearate, stearic acid and the like. Preferred liquid carriers are phosphate buffered saline solution, syrup, oil such as peanut oil and olive oil, water, emulsions, various types of wetting agents, sterile solutions and the like. Similarly, the carrier may include time delay material well known to the art, such as glyceryl mono-stearate or glyceryl di-stearate alone or with a wax. Further suitable carriers are well known in the art, see, e.g., Remington's Pharmaceutical Sciences, Mack Publishing Company, Easton, Pa.

The diluent is, preferably, selected so as not to affect the biological activity of the combination. Preferred diluents are distilled water, physiological saline, Ringers solutions, dextrose solution, and Hank's solution.

The pharmaceutical composition or formulation, preferably, may comprise more than one of the aforementioned carriers or diluents as well as other components such as adjuvants or non-toxic, non-therapeutic, non-immunogenic stabilizers and the like.

A therapeutically effective dosage or amount refers to an amount of trans-4-tert-butyl cyclohexanol in a pharmaceutical composition of the present invention which prevents, ameliorates or treats the symptoms accompanying a disease or condition referred to in this specification.

Moreover, a therapeutically effective dosage can be also described by the IC50 value, i.e. the amount of a therapeutically active compound which is required to achieve half of the maximum inhibition for an enzyme or signalling molecule, such as TRPV1 in the present case.

The dosage regimen will be determined by the attending physician and other clinical factors; preferably in accordance with any one of the above described methods. As is well known in the medical arts, dosages for any one patient depends upon many factors, including the patient's size, body surface area, age, sex, time and route of administration, general health, and other drugs being administered concurrently. Progress can be monitored by periodic assessment.

The pharmaceutical composition referred to herein are administered at least once in order to treat or ameliorate or prevent a disease or condition recited in this specification. However, the said pharmaceutical compositions may be administered more than one time, for example from one to four times daily up to a non-limited number of days.

The pharmaceutical composition of the present invention can be formulated as a capsule, sachet, cachet, paper or other suitable container or vehicle. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient. The aforementioned carriers or diluents may be present in amounts of 1 to 99% weight (w/w) or even more, preferably of 10 to 80% weight (w/w) based on the total weight of the envisaged composition. The required amounts of the substances or additives can be determined by those skilled in the art without further ado, e.g. by trial and error, dependent on the envisaged formulation and its application provided that the formulation provides a therapeutically effective dosage of trans-4-tert-butyl cyclohexanol as discussed above.

Moreover, trans-4-tert-butyl cyclohexanol can be administered in combination with other substances, such as drugs or cosmetic agents, either in a common pharmaceutical composition or as separated pharmaceutical compositions wherein said separated pharmaceutical compositions may be provided in form of a kit of parts.

The present invention also contemplates trans-4-tert-butyl cyclohexanol to be used for treating or preventing a pain condition or the use of trans-4-tert-butyl cyclohexanol for the manufacture of a pharmaceutical composition for treating or preventing a pain condition.

The present invention thus also relates to trans-4-tert-butyl cyclohexanol for treating or preventing a pain condition.

The term "pain condition" as used herein refers to an unpleasant sensory and emotional experience associated with actual or potential tissue damage or described in terms of such damage. The said experience is caused by stimulation of specific nerve sensors also called nociceptors. Pain is a defense reaction of the body which also triggers or encompasses biological counteractions, i.e. a pain condition is characterized by efferent as well as afferent nervous actions. The vanilloid receptor TRPV1 plays a central role as multiple pain stimuli integrator. The receptor is a nonselective cation channel found in polymodal sensory neurons. It can be activated by various physical or chemical pain stimuli such as heat, noxious compounds or inflammatory molecules (see Szallasi in Nature Rev Drug Discovery 2007, 6: 357-372; Patapoutian in Nature Rev Drug Discovery 2009, 8: 55-68). Inhibition of TRPV1 was shown to be efficient in pain treatment (WO 2006/031852, WO 2007/076104, US 2005/0176726). Accordingly, a pain condition according to the present invention, preferably, refers to a disease or disorder involving sensory nerve action mediated by TRPV1.

A pain condition according to the present invention, thus, may be a sensory experience of "classical" pain in the central nervous system but also a pain associated neurogenic reaction, such as skin inflammation or irritation. Preferably, the said pain condition is selected from the group consisting of: somatic pain, inflammatory pain, visceral pain, neuropathic pain, dental pain, general headache, migraine, cluster headache, mixed-vascular and non-vascular syndromes, tension headache, general inflammation, neurogenic inflammation, irritation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders and bladder disorders.

From the above, it follows that trans-4-tert-butyl cyclohexanol is applied in a method for treating or preventing a pain condition in a subject suffering therefrom comprising administering a therapeutically effective amount of trans-4-tert-butyl cyclohexanol to the said subject.

Advantageously, it has been found in the studies underlying the present invention that trans-4-tert-butyl cyclohexanol can be successfully applied for treating pain conditions and symptoms accompanied therewith, in particular, the pain conditions mediated by receptor TRPV1. Specifically, antagonistic activity for TRPV1 was demonstrated in cell culture for trans-4-tert-butyl cyclohexanol.

The present invention also relates to the use of trans-4-tert-butyl cyclohexanol for the manufacture of a pharmaceutical composition for treating or preventing a pain condition as well as to a method for treating or preventing a pain condition in a human being suffering therefrom comprising administering a therapeutically effective amount of trans-4-tert-butyl cyclohexanol to said human being, wherein said pain condition preferably is selected from the group consisting of: somatic pain, inflammatory pain, visceral pain, neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders and bladder disorders.

A further aspect of the present invention relates to formulations according to the invention in the form of oral care products (oral hygiene products), wherein the oral care product is preferably in the form of toothpaste, dental cream, dental gel, dental powder, tooth-cleaning liquid, tooth-cleaning foam, mouthwash, dental cream and mouthwash as a 2-in-1 product, sweet for sucking, mouth spray, dental silk or dental care chewing gum. The activity of the formulations according to the invention also manifests itself remarkably well in the field of oral hygiene. A bad breath-reducing activity of the formulations according to the invention has moreover been found in our own studies.

Dental care compositions (as a preferred example of an oral care product according to the invention) in general comprise an abrasive system (abrasive or polishing agent), such as e.g. silicas, calcium carbonates, calcium phosphates, aluminium oxides and/or hydroxyapatites, surface-active substances, such as e.g. sodium lauryl sulfate, sodium lauryl sarcosinate and/or cocamidopropyl betaine, moisture-retaining agents, such as e.g. glycerol and/or sorbitol, thickening agents, such as e.g. carboxymethylcellulose, polyethylene glycols, carrageenan and/or Laponite®, sweeteners, such as e.g. saccharin, flavour correctants for unpleasant taste impressions, flavour correctants for further, as a rule not unpleasant taste impressions, flavour-modulating substances (e.g. inositol phosphate, nucleotides, such as guanosine monophosphate, adenosine monophosphate or other substances, such as sodium glutamate or 2-phenoxypropionic acid), cooling agents, such as e.g. menthol derivatives (e.g. L-menthyl lactate, L-menthyl alkyl carbonates, menthone ketals, menthanecarboxylic acid amides), 2,2,2-trialkylacetic acid amides (e.g. 2,2-diisopropylpropionic acid methylamide), icilin and icilin derivatives, stabilizers and active compounds, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, aromas, sodium bicarbonate and/or odour correctants.

Formulations according to the invention in the form of chewing gums or dental care chewing gums comprise chewing gum bases which comprise elastomers, such as, for example, polyvinyl acetates (PVA), polyethylenes, (low or medium molecular weight) polyisobutenes (PIB), polybutadienes, isobutene-isoprene copolymers (butyl rubber), polyvinyl ethyl ethers (PVE), polyvinyl butyl ethers, copolymers of vinyl esters and vinyl ethers, styrene/butadiene copolymers (styrene/butadiene rubber, SBR) or vinyl elastomers, e.g. based on vinyl acetate/vinyl laurate, vinyl acetate/vinyl stearate or ethylene/vinyl acetate, and mixtures of the elastomers mentioned, as described, for example, in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases comprise further constituents, such as, for example, (mineral) fillers, plasticizers, emulsifiers, antioxidants, waxes, fats or fatty oils, such as, for example, hardened (hydrogenated) plant or animal fats, and mono-, di- or triglycerides. Suitable (mineral) fillers are, for example, calcium carbonate, titanium dioxide, silicon dioxide, talc, aluminium oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate) and triethyl citrate. Suitable waxes are, for example, paraffin waxes, candelilla wax, carnauba wax, microcrystalline waxes and polyethylene waxes. Suitable emulsifiers are, for example, phosphatides, such as lecithin, and mono- and diglycerides of fatty acids, e.g. glycerol monostearate.

Formulations according to the invention (in particular those which are in the form of an oral care product) preferably additionally comprise one or more aroma and/or flavouring substances, such as essential oils and extracts, tinctures and balsams, such as, for example, anisole, basil oil, bergamot oil, bitter almond oil, camphor oil, citronella oil, lemon oil; Eucalyptus citriodora oil, eucalyptus oil, fennel oil, grapefruit oil, ginger oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the formulations according to the invention comprise at least one aroma substance, preferably 2, 3, 4, 5, 6, 7, 8, 9, 10 or more aroma substances, chosen from the following group: menthol (preferably l-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanel, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, trans-sabinene hydrate, menthofuran, caryophyllene, germacrene D, cinnamaldehyde, mint lactone, thymol, gamma-octalactone, gamma-nonalactone, gamma-decalactone, (1,3E,5Z)-undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

Particularly preferred cooling agents for oral care compositions according to the present invention comprise one or more cooling agents selected from the group consisting of: menthone glycerol acetal (trade name: Frescolat®MGA), menthyl lactate (preferably l-menthyl lactate, in particular l-menthyl l-lactate, trade name: Frescolat®ML), substituted menthyl-3-carboxylic acid amides (e.g. menthyl-3-carboxylic acid N-ethylamide), 2-isopropyl-N-2,3-trimethylbutanamide, 3-menthoxypropane-1,2-diol, 2-hydroxyethyl menthyl carbonate, 2-hydroxypropyl menthyl carbonate, isopulegol, monomenthyl succinate and monomenthyl glutarate.

Formulations according to the invention which comprise l-menthol and at least one, particularly preferably at least two cooling substances are preferred according to the invention.

The invention likewise provides a cosmetic or therapeutic method for prophylaxis of skin irritation, with the following steps:
provision of a formulation according to the invention or of a medicament according to the invention and
application of the formulation or of the medicament to non-irritated skin in an active amount.

The invention furthermore provides a cosmetic or therapeutic method for treatment of skin irritation, with the following steps:
provision of a formulation according to the invention or of a medicament according to the invention and
application of the formulation or of the medicament to irritated skin in an active amount.

The invention furthermore provides a method for prophylaxis of the skin-irritating action or for reducing, eliminating or suppressing the skin-irritating action of a substance or substance mixture, with the following steps:
a) provision of a substance or substance mixture having a skin-irritating action,
b) provision of trans-4-tert-butyl cyclohexanol or a cosmetically or pharmaceutically acceptable salt thereof, in particular the $Na^+$, $K^+$, $NH_4^+$, $Mg^{2+}$ or $Ca^{2+}$ salt, or of a composition or a medicament according to the invention,
c) bringing together the substances of a) and b), so that the skin-irritating action is reduced, eliminated or suppressed and another composition or medicament according to the invention is formed.

The present invention also relates to the use of a formulation, a product or a medicament according to the present invention
for prophylaxis of skin irritation and/or for treatment of skin irritation for medical and/or other than medical purposes, and/or
for reducing, eliminating or suppressing the skin-irritating action of a substance or substance mixture.

One advantage of the method according to the invention mentioned last is that the skin-irritating action of substances or substance mixtures can be moderated in this way to the extent that they are accessible for uses for which they were hitherto not available. On the basis of the method according to the invention mentioned last, higher concentrations of skin-irritating substances and substance mixtures can also be employed in uses where there is the possibility of skin contact. In this context, it is particularly preferable if, on the basis of the method according to the invention mentioned last, the skin-irritating action of the skin-irritating compound is eliminated completely (i.e. it no longer exists) or is suppressed completely (i.e. it no longer has an effect). The method according to the invention mentioned last can be employed, for example, against the skin-irritating action of detergents and allergy-inducing substances.

Preferred embodiments and further aspects of the present invention emerge from the attached patent claims and the following examples, the examples not being intended to limit the invention. Unless indicated otherwise, all data, in particular percentages, refer to the weight.

Unless indicated otherwise racemic trans-4-tert-butyl cyclohexanol (purity >96 wt. %, amount of racemic cis-isomer <4 wt. %) was used in the following examples, obtainable as described in Organic Syntheses Collective Volume 5, 175-178, Wiley, New York, 1973 or J. Am. Chem. Soc. 1955, 77, 5562-5578.

EXAMPLE 1

In Vitro Assays and In Vivo Testing

A commercially available mixture consisting of 28% cis-4-tert-butyl cyclohexanol and 72% trans-4-tert-butyl cyclohexanol was purified via preparative HPLC to obtain the essentially pure cis- and trans-isomers of 4-tert-butyl cyclohexanol.

EXAMPLE 1.1

In Vitro Assays

Three samples of cis- and/or trans-4-tert-butyl cyclohexanol were assessed: 1) 99% trans-isomer, 2) an isomeric mixture enriched in the cis-isomer (59% cis, 41% trans) and 3) 99% cis-isomer.

Assay Conditions:
Calciumassay based on fluorescent dye Fluo-4-AM
Negative Control: KH-buffer (solvent)
Positive Control: Ionomycin (generell calcium induction)
Positive Control Capsaicin (natural agonist of TRPV1)

One day prior to performing the assay, HEK293 cells stably overexpressing recombinant human TRPV1 were plated onto black-walled assay plates, at a density of 45,000 cells per well. Using the FLEX Station system the change of the cellular calcium concentration (calcium influx) induced by TRPV1 activation was monitored using the calcium sensitive fluorescent dye fluo-4 (494 nm/516 nm (exitation/emission)). The pharmacological TRPV1 antagonist Ruthenium Red (1 µM) was used as positive control [J. Biol. Chem. 2004, 279 (34): 35741-8]. The dye-loaded stable cells in plates were placed into the fluorescence microtiter plate reader to monitor fluorescence (excitation 488 nm, emission 520 nm) change after the addition of 50 µl assay buffer (118 mM NaCl; 4.7 mM KCl; 1.2 mM $MgSO_4$; 1.2 mM $KH_2PO_4$; 4.2 mM $NaHCO_3$; 1.3 mM $CaCl_2$; 10 mM HEPES (N-(2-hydroxyethyl)-piperazine-N'-2-ethanesulfonic acid) (pH: 7.4)) supplemented with an antagonist. Calcium mobilization was quantified as the change of peak fluorescence ($\Delta F$) over the baseline level (F). The analysis was done with the software of the microtiter plate reader (FLEX Station). Potential TRPV1 antagonists were tested at an effective range of 0.5-50 µM. The test compounds were either applied in parallel to 30 nM capsaicin or 10 min prior to the agonist. TRPV1 antagonists were tested for their antagonistic activity in the presence of 30 nM capsaicin, which is the $EC_{80}$ effective capsaicin concentration leading to 80% of the maximum capsaicin dependent TRPV1 activation.

EXAMPLE 1.1.A

Antagonistic efficacy of the isomers of 4-tert-butyl cyclohexanol on transient receptor potential ion channel 1 in cell based fluorescent analysis.

The three samples were tested for TRPV1 antagonism at parallel application with capsaicin as agonist. Sample 1, i.e. the pure trans-isomer was significantly more active ($IC_{50}$=34.1 µM) than sample 2) ($IC_{50}$=86.9 µM), whereas sample 3), i.e. the pure cis-isomer, was inactive.

EXAMPLE 1.1.B

TRPV1 antagonist in vitro at incubation prior to capsaicin: cis-4-tert-butyl cyclohexanol and trans-4-tert-butyl cyclohexanol were applied to HEK293 cells 10 min before capsaicin treatment.

The sequence of application of antagonist and agonist can significantly influence the antagonist efficacy [Mol. Pharmacol. 2006, 69(4):1166-73]. We therefore additionally tested the pure cis- and trans-isomers of 4-tert-butyl cyclohexanol respectively in a pre-incubation mode with application of the respective isomer 10 min before addition of capsaicin. However, this experiment did not reveal any difference to the parallel incubation mode and it was confirmed that the cis-isomer was not active.

EXAMPLE 1.2

In Vivo Testing

A study was performed with 9 volunteers who were sensitive to capsaicin. A freshly prepared solution of 31.6 ppm capsaicin (which proved to be the most appropriate concentration: clear stinging perception without erythema or burn feeling) in PBS (phosphate buffered saline) was applied to the left and right upper cheek bone area with a cotton tip with smooth rubbing. After 60 seconds all participants sensed a pronounced stinging effect. Then, an O/W-emulsion with 1 wt. % racemic trans-4-tert-butyl cyclohexanol (purity >99 wt. %) was applied on one cheek and the placebo O/W-emulsion on the other cheek (blinded samples). The stinging effect was evaluted 5 minutes later on the following scale: 0 (no effect), 1 (stinging slightly reduced), 2 (stinging moderately reduced), 3 (stinging strongly reduced by still some stinging perceptible), and 4 (stinging completely suppressed).

The TRPV1 antagonist (trans-4-tert-butyl cyclohexanol) was rated an average of 3.10 on said scale (for placebo: 0.25) and inhibited the stinging sensation with very high significance ($p<0.000013$).

EXAMPLE 1.3

Clinical Studies

A study was performed with 20 volunteers who were sensitive to capsaicin. The following freshly prepared mixtures were assessed by application to the nasolabial fold (blinded samples): c1-O/W-emulsion comprising 31.6 ppm capsaicin, c2-O/W-emulsion comprising 31.6 ppm capsaicin and 1 wt. % racemic trans-4-tert-butyl cyclohexanol (purity >99 wt. %) and control—PBS. On day 1 sample c2 was assessed versus control. On day 2 sample c1 was assessed versus control. The stinging and burning effects were evaluted 3 minutes later on the same scale as in Example 1.2.

The TRPV1 antagonist (trans-4-tert-butyl cyclohexanol) was rated an average of 2.95 on said scale (for placebo: 0.35) and inhibited/reduced both stinging and burning sensation with high significance ($p<0.001$). The rating for trans-4-tert-butyl cyclohexanol regarding inhibition/reduction for the sum of all sensations stinging, burning, tingling, tickling and skin tightness were confirmed with very high significance ($p<0.0001$).

Similar results were obtained when using a skin whitening agent (a resorcinol derivative described e.g. in WO 2007/077260) instead of capsaicin as agonist, which induced a stinging sensation on the sensitive skin of the 20 volunteers who participated in this study.

EXAMPLE 2

Concentrated Compositions According to the Present Invention

Formulation Examples 1-10: Formulations comprising trans-4-tert-butyl cyclohexanol according to the present invention having a skin irritation-reducing action Formulation Example 1: Skin-lightening day cream O/W Formulation Example 2: Skin-soothing lotion with plant extracts O/W Formulation Example 3: Aftersun Balm Formulation Example 4: Body Spray Formulation Example 5: Sunscreen lotion (O/W), broadband protection Formulation Example 6: W/O night cream Formulation Example 7: Shampoo Formulation Example 8: Self-Tanning Cream Formulation Example 9: Barrier repair cream O/W Formulation Example 10: Antiperspirant/deodorant roll-on The following Fragrance "WHITE" was used in Formulation Examples 1-10:

Fragrance "WHITE": Perfume Oil with White Blossom Smell

| Component/NAME | Parts by weight |
| --- | --- |
| Benzyl acetate | 60.00 |
| Citronellyl acetate | 60.00 |
| Cyclamene aldehyde (2-methyl-3-(4-isopropylphenyl)propanal | 20.00 |
| Dipropylene glycol (DPG) | 60.00 |
| Ethyl linalool | 40.00 |
| Florol (2-isobutyl-4-methyltetrahydro-2H-pyran-4-ol) | 30.00 |
| Globanone [(E/Z)-8-cyclohexadecen-1-one] | 180.00 |
| Hedione (methyldihydrojasmonate) | 140.00 |
| Hexenyl Isalicylate, cis-3 | 10.00 |
| Vertocitral (2,4-dimethyl-3-cyclohexene carboxaldehyde) | 5.00 |
| Hydratropa aldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalylacetate | 30.00 |
| Methylbenzoate, 10% in DPG | 25.00 |
| para-methyl cresol, 10% in DPG | 10.00 |
| Nerol | 20.00 |
| Phenylpropyl aldehyde | 5.00 |
| 2-Phenylethyl alcohol | 82.00 |
| Tetrahydrogeraniol | 13.00 |
| 2,2-dimethyl-3-cyclohexyl-1-propanol | 80.00 |

| | CC-1 (wt. %) | CC-2 (wt. %) | CC-3 (wt. %) | CC-4 (wt. %) | CC-5 (wt. %) | CC-6 (wt. %) | CC-7 (wt. %) |
| --- | --- | --- | --- | --- | --- | --- | --- |
| trans-4-tert-butyl cyclohexanol | 22.50 | 33.33 | 30.00 | 38.50 | 25.00 | 35.50 | 28.50 |
| 1,2-butylene glycol | 77.50 | — | — | — | — | — | 31.50– |
| 1,2-pentanediol | — | 66.67 | 35.00 | — | 75.00 | 50.00 | 40.00 |
| 1,2-hexanediol | — | — | 35.00 | — | — | 14.50 | — |
| dipropylene glycol | — | — | — | 61.50 | — | — | — |

| RAW MATERIAL NAME (MANUFACTURER) | INCI | % BY WEIGHT/FORMULATION EXAMPLE | | | | | | | | | |
|---|---|---|---|---|---|---|---|---|---|---|---|
| | | 1 | 2 | 3 | 4 | 5 | 6 | 7 | 8 | 9 | 10 |
| trans-4-tert-butyl cyclohexanol | | 1.0 | 0.8 | 1.1 | 0.4 | 0.55 | 1.75 | 0.3 | 1.0 | 1.25 | 0.75 |
| -(-Alpha-)-Bisabolol, natural (Symrise) | Bisabolol | 0.3 | | | 0.1 | 0.3 | 0.2 | | | | 0.1 |
| Ginger $CO_2$ Extract (Flavex) | *Zingiber Officinale* (Ginger) Root Extract | | | 0.003 | 0.005 | 0.003 | | | | | |
| Abil 350 (Degussa-Goldschmidt) | Dimethicone | 0.5 | 2.0 | 1.0 | | | | | 0.5 | 0.5 | |
| Allantoin (Merck) | Allantoin | | 0.2 | 0.1 | | | | | | 0.25 | |
| Aloe Vera Gel Concentrate 10/1 (Symrise) | Water (Aqua), *Aloe Barbadensis* Leaf Juice | | | 3.0 | | 3.0 | | 0.45 | | | |
| Alugel 34 TH (Baerlocher) | Aluminium Stearate | | | | | | 1.0 | | | | |
| Aqua-Ceramide (Kao) | Cetyloxypropyl Glyceryl Methoxypropyl Myristamide | | 0.1 | | | | | | | | 0.1 |
| Arbutin (Sabinsa) | β-Arbutin | 0.2 | | | | | | | | | |
| 4-(1-phenylethyl)-1,3-benzenediol | | 0.5 | | | | | | | | | |
| Sodium Ascorbyl Phosphate (EMD Chemicals) | Sodium Ascorbyl Phosphate | 2.0 | | 1.0 | | | | | | | |
| Butylene Glycol | Butylene Glycol | | | 5.0 | | | | | | | |
| Carbopol ETD 2050 (Noveon) | Carbomer | | | | | | 0.2 | | | | |
| Carbopol Ultrez-10 (Noveon) | Carbomer | | 0.1 | | | | | | | | |
| Ceramide 2 (Sederma) | Ceramide 2 | 0.1 | | | | | | | | | |
| Ceramide PC104 (Pacific Corporation) | Hydroxypropyl Bispalmitamide MEA | | | | | 0.1 | | | | | |
| Ceramide SL (Sino Lion) | Hydroxyethyl Palmityl Oxyhydroxypropyl Palmitamide | | | | | | | 0.1 | | | |
| Cetiol OE (Cognis) | Dicaprylyl Ether | | | 4.0 | | | | | | | |
| Cetiol SB 45 (Cognis) | *Butyrospermum Parkii* (Shea Butter) | | | 1.0 | | | | | | | |
| Citric Acid 10% sol. | Citric Acid | | | | | | | | 0.3 | | |
| Comperlan 100 (Cognis) | Cocamide MEA | | | | | | | | 0.5 | | |
| Dihydroxyacetone (Merck) | Dihydroxyacetone | | | | | | | | | 5.0 | |
| Dow Corning 246 Fluid (Dow Corning) | Cyclohexasiloxane and Cyclopentasiloxane | | | | | 2.0 | | | | | |

-continued

| RAW MATERIAL NAME (MANUFACTURER) | INCI | % BY WEIGHT/FORMULATION EXAMPLE | | | | | | | | | |
|---|---|---|---|---|---|---|---|---|---|---|---|
| | | 1 | 2 | 3 | 4 | 5 | 6 | 7 | 8 | 9 | 10 |
| Dow Corning 345 Fluid (Dow Corning) | Cyclomethicone | | | | 0.5 | | | | | | |
| D-Panthenol (BASF) | Panthenol | | | 1.0 | | | | | | | |
| Dracorin CE (Symrise) | Glyceryl Stearate Citrate | 5.0 | | | | | | | 5.0 | 1.5 | |
| Dracorin GMS (Symrise) | Glyceryl Stearate | | 2.0 | | | | | | | 2.0 | |
| Dracorin GOC (Symrise) | Glyceryl Oleate Citrate, Caprylic/Capric Triglyceride | | | | 2.0 | | | | | | |
| Drago-Beta-Glucan (Symrise) | Water (Aqua), Butylene Glycol, Glycerin, *Avena Sativa* (Oat), Kernel Extract | 0.3 | | | | | | | | | |
| Dragocid Liquid (Symrise) | Phenoxyethanol, Methylparaben, Ethylparaben, Butylparaben, Propylparaben, Isobutylparaben | | 0.8 | 0.7 | | 0.7 | 0.8 | | | 0.8 | |
| Dragoderm (Symrise) | Glycerin, *Triticum Vulgare* (Wheat) Gluten, Water (Aqua) | | | | | | | | 2.0 | | |
| Drago-Oat-Active (Symrise) | Water (Aqua), Butylene Glycol, *Avena Sativa* (Oat) Kernel Extract | | | | 1.0 | | | | | | |
| Dragosan W/O Liquid (Symrise) | Polyglyceryl-3-Polyricinoleate, Sorbitan Isostearate | | | | | | 1.0 | | | | |
| Dragosan W/O P (Symrise) | Sorbitan Isostearate, Hydrogenated Castor Oil, Ceresin, Beeswax (*Cera Alba*) | | | | | | 6.0 | | | | |
| Dragoxat EH (Symrise) | Ethylhexyl Ethylhexanoate | 3.0 | 3.0 | | 4.0 | | | | 3.0 | | |
| Dragoxat 89 (Symrise) | Ethylhexyl Ethylisononanoate | | | | | | | | | 2.0 | |
| EDETA B Powder (BASF) | Tetrasodium EDTA | | | | | | | 0.1 | | | |
| EDETA DB (BASF) | Disodium EDTA | | | | | 0.1 | | | 0.1 | | |
| Emulsiphos (Symrise) | Potassium Cetyl Phosphate, Hydrogenated Palm Glycerides | | 2.0 | | | 1.5 | | | | 2.0 | |
| Ethanol 96% | Ethanol | | | | | | | | | 2.0 | 30.0 |
| Extrapone Green Tea GW (Symrise) | Glycerin, Water (Aqua), *Camellia Sinensis* Leaf Extract | | | 0.2 | | | | | | | |

-continued

| RAW MATERIAL NAME (MANUFACTURER) | INCI | % BY WEIGHT/FORMULATION EXAMPLE | | | | | | | | | |
|---|---|---|---|---|---|---|---|---|---|---|---|
| | | 1 | 2 | 3 | 4 | 5 | 6 | 7 | 8 | 9 | 10 |
| Extrapone Witch Hazel Distillate colourless (Symrise) | Propylene Glycol, *Hamamelis Virginiana* (Witch Hazel) Water, Water (Aqua), *Hamamelis Virginiana* (Witch Hazel) Extract | | | | | | 1.0 | | | | |
| Extrapone Rosemary GW (Symrise) | Glycerin, Water (Aqua), *Rosmarinus officinalis* (Rosemary) Leaf Extract | | 0.3 | | | | | | | 0.5 | |
| Farnesol (Symrise) | Farnesol | | | | | | | | | | 0.5 |
| Frescolat MGA. (Symrise) | Menthone Glycerol Acetal | 0.5 | | | | 0.3 | | | | | |
| Frescolat ML cryst. (Symrise) | Menthyl Lactate | | | 0.8 | | | | | | | 0.2 |
| Genapol LRO liquid (Cognis) | Sodium Laureth Sulfate | | | | | | | 37.0 | | | |
| Givobio GZN (Seppic) | Zinc Gluconate | | | | | | | | | 0.5 | |
| Glycerol 85% | Glycerin | 3.0 | 2.0 | 4.0 | | 4.7 | 2.0 | | 1.5 | 3.0 | |
| Hydrolite-5 (Symrise) | Pentylene Glycol | | | | 5.0 | | | | 3.5 | | |
| Hydroviton (Symrise) | Water, Glycerin, Sodium Lactate, TEA Lactate, Serine, Lactic Acid, Urea, Sorbitol, Sodium Chloride, Lauryl Diethylenediaminoglycine, Lauryl Aminopropylglycine, Allantoin | | | | | | | | | 1.0 | |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropyl palmitate (Symrise) | Isopropyl Palmitate | 4.0 | | | | | | | 4.0 | | |
| Karion F (Merck) | Sorbitol | | | | | | 2.0 | | | | |
| Keltrol RD (CP-Kelco) | Xanthan Gum | 0.2 | 0.1 | | | | | | | | |
| Keltrol T (Danby-Chemie) | Xanthan Gum | | | | | 0.2 | | | 0.3 | | |
| Kojic acid (Cosmetochem) | Kojic Acid | 1.0 | | | | | | | | | |
| Lanette 16 (Cognis) | Cetyl Alcohol | 1.0 | | | | | | | 1.0 | | |
| Lanette O (Cognis) | Cetearyl Alcohol | | 3.0 | | | 1.0 | | | | 2.0 | |
| Lara Care A-200 (Rahn) | Galactoarabinan | | | 0.3 | | | | | | | |

-continued

| RAW MATERIAL NAME (MANUFACTURER) | INCI | % BY WEIGHT/FORMULATION EXAMPLE | | | | | | | | | |
|---|---|---|---|---|---|---|---|---|---|---|---|
| | | 1 | 2 | 3 | 4 | 5 | 6 | 7 | 8 | 9 | 10 |
| Magnesium Chloride (Merck) | Magnesium Chloride | | | | | | 0.7 | | | | |
| Merquat 550 (Ondeo Nalco) | Polyquaternium-7 | | | | | | | 0.5 | | | |
| NaOH 10% sol. | Sodium Hydroxide | | | | | | | | | 0.3 | |
| Naringin (Exquim) | 4',5,7-Trihydroxyflavone7-O-Neohesperidoside | | | | | | | 0.5 | 2.0 | | |
| Sodium benzoate | Sodium Benzoate | | | | | | | 0.5 | | | |
| Natrosol 250 HHR (Aqualon) | Hydroxyethyl-cellulose | | | | | | | | | | 0.3 |
| Neo Heliopan 357 (Symrise) | Butyl Methoxy-dibenzoyl-methane | | | | | 1.0 | | | | | |
| Neo Heliopan AP (Symrise) (10% as sodium salt) | Disodium Phenyl Dibenzimidazole Tetrasulfonate | | | | | 10 | | | | | |
| Neo Heliopan AV (Symrise) | Ethylhexyl Methoxy-cinnamate | 5.0 | | | | 3.0 | | | | | |
| Neo Heliopan Hydro (Symrise) (15% as sodium salt) | Phenylbenz-imidazole Sulfonic Acid | | | | | 6.7 | | | | | |
| Neo Heliopan MBC (Symrise) | 4-Methylbenzyl-idene Camphor | | | | | 1.5 | | | | | |
| Neo Heliopan OS (Symrise) | Ethylhexyl Salicylate | | | | | 5.0 | | | | | |
| Neutral Oil | Caprylic/Capric Triglyceride | 6.0 | | | 4.0 | 2.0 | | | 6.0 | 10.0 | |
| Oxynex 2004 (Merck) | BHT | | | | | | 0.1 | | | | |
| Paraffin oil 5 Grade E (Parafluid) | Paraffinum Liquidum | | | | 4.0 | | | | | | |
| PCL Liquid 100 (Symrise) | Cetearyl Ethylhexoate | 3.0 | 5.0 | | 7.0 | | | | | | |
| PCL Solid (Symrise) | Stearyl Heptanoate, Stearyl Caprylate | | 2.0 | | | | | | | | |
| PCL-Liquid (Symrise) | Cetearyl Ethylhexanoate, Isopropyl Myristate | | | | | | | 12.0 | 3.0 | | |
| Pemulen TR-2 (Noveon) | Acrylates/C10-30 Alkyl Acrylate Crosspolymer | | | 0.3 | 0.2 | | | | | | |
| 4-(1-Phenylethyl)-1,3-benzenediol | 4-(1-Phenylethyl)-1,3-benzenediol | 0.5 | | | | | | | | | |
| 1,2-Propylene Glycol 99P GC | Propylene Glycol | | | 5.0 | | | | | | | |

-continued

| RAW MATERIAL NAME (MANUFACTURER) | INCI | % BY WEIGHT/FORMULATION EXAMPLE | | | | | | | | | |
|---|---|---|---|---|---|---|---|---|---|---|---|
| | | 1 | 2 | 3 | 4 | 5 | 6 | 7 | 8 | 9 | 10 |
| Pseudo-ceramide 391 | N-(1-Hexadecanoyl)-4-hydroxy-L-proline (1-hexadecyl)ester | | 0.1 | | | | | 0.2 | | 0.5 | |
| Retinyl Palmitate in Oil (DSM Nutrional Products) | Retinyl Palmitate | | | | | | 0.2 | | | | |
| Sepigel 305 | Polyacrylamide, C13-14 Isoparaffin, Laureth-7 | | | | | | | | 1.0 | | |
| Sodium Chloride | Sodium Chloride | | | | | | | 1.0 | | | |
| Sodium Hydroxide (10% sol.) | Sodium Hydroxide | | | 0.3 | 0.6 | 0.4 | | | | | |
| Solubilizer 611674 (Symrise) | PEG-40 Hydrogenated Castor Oil, Trideceth-9, Water (Aqua) | | | | | | | | | | 2.0 |
| Sun Flower Oil (Wagner) | Helianthus Annuus (Sunflower) Seed Oil | | | | | | 5.0 | | | | |
| Sweet Almond Oil (Wagner) | Prunus dulcis | | | | | | 5.0 | | | | |
| SymMatrix (Symrise) | Maltodextrin, Rubus Fruticosus (Blackberry) Leaf Extract | | 0.1 | | | 0.3 | 1.0 | | | | |
| Symdiol 68 (Symrise) | 1,2-Hexanediol, Caprylylglycol | 0.5 | | | | | | | | | |
| Fragrance "WHITE" (Symrise) | Fragrance | 0.3 | 0.3 | 0.3 | 0.2 | 0.4 | 0.4 | 0.5 | 0.3 | 0.3 | 1.0 |
| Tamasterol (Tama Biochemicals) | Phytosterols | | | | | | | | | 0.3 | |
| Tego Betain L7 (Degussa) | Cocamidopropyl Betaine | | | | | | | | 6.0 | | |
| Tegosoft PC 31(Degussa) | | | | | | | | | | 0.3 | |
| Tegosoft TN (Degussa) | C12-15 Alkyl Benzoate | | | 5.0 | | 5.0 | | | | | |
| Triethanolamine, 99% | Triethanolamine | | | | | 0.5 | | | | | |
| Tocopherol Acetate (DSM Nutritional Products) | Tocopheryl Acetate | | 0.5 | | 0.5 | | 3.0 | | | 0.3 | |
| Zirkonal L 450 (BK Giulini) | Aluminium Zirconium Pentachlorohydrate (40% aqueous solution) | | | | | | | | | | 37.0 |
| Water, demineralized | Water (Aqua) | to 100 | to 100 | to 100 | to 100 | to 100 | to 100 | to 100 | to 100 | to 100 | to 100 |

Formulation Examples 11-16: Oral hygiene/orally applicable medicinal products

The following Peppermint Flavor PF1 was used in Formulation Examples 11, 13 and 15:

| Peppermint Flavor PF1 | parts by weight |
|---|---|
| Isobutyraldehyde | 0.5 |
| 3-Octanol | 0.5 |
| Dimethyl sulphide | 0.5 |
| trans-2-Hexenal | 1.0 |
| cis-3-Hexenol | 1.0 |
| 4-Terpineol, natural | 1.0 |
| Isopulegol | 1.0 |
| Piperitone, natural, from eucalyptus | 2.0 |
| Linalool | 3.0 |
| 8-Ocimenyl acetate, 10% in triacetin | 5.0 |
| Isoamyl alcohol | 10.0 |
| Isovaleraldehyde | 10.0 |
| alpha-Pinene, natural | 25.0 |
| beta-Pinene, natural | 25.0 |
| Neomenthol, racemic | 40.0 |
| Eucalyptol (1,8-cineol), natural | 50.0 |
| L-Menthyl acetate of the formula D | 70.0 |
| L-Menthone | 220.0 |
| D-Isomenthone | 50.0 |
| L-Menthol | 483.5 |
| Nonenolide | 1.0 |

Formulation Example 11: Gel dental cream

| | I (%) | II (%) | III (%) |
|---|---|---|---|
| Na carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Na saccharinate | 0.07 | 0.07 | 0.07 |
| Na fluoride | 0.24 | 0.24 | 0.24 |
| p-Hydroxybenzoic acid (PHB) ethyl ester | 0.15 | 0.15 | 0.15 |
| Peppermint flavor PF1 | 1.00 | 1.00 | 1.00 |
| trans-4-tert-butyl cyclohexanol | 0.50 | 0.90 | 1.50 |
| Abrasive silica | 11.00 | 11.00 | 11.00 |
| Thickening silica | 6.00 | 6.00 | 6.00 |
| Sodium dodecyl sulfate (SDS) | 1.40 | 1.40 | 1.40 |
| Dist. water | to 100.00 | to 100.00 | to 100.00 |

Formulation Example 12: Dental cream against plaque

| | I (%) | II (%) | III (%) |
|---|---|---|---|
| Carrageenan | 0.90 | 0.90 | 0.90 |
| Glycerin | 15.00 | 15.00 | 15.00 |
| Sorbitol 70%, in water | 25.00 | 25.00 | 25.00 |
| PEG 1000 | 3.00 | 3.00 | 3.00 |
| Na fluoride | 0.24 | 0.24 | 0.24 |
| Tetrapotassium diphosphate | 4.50 | 4.50 | 4.50 |
| Tetrasodium diphosphate | 1.50 | 1.50 | 1.50 |
| Na saccharinate | 0.40 | 0.40 | 0.40 |
| Precipitated silica | 20.00 | 20.00 | 20.00 |
| Titanium dioxide | 1.00 | 1.00 | 1.00 |
| PHB methyl ester | 0.10 | 0.10 | 0.10 |
| Spearmint flavor (comprising 60 wt. % l-carvone and 25 wt. % l-menthol) | 1.00 | 1.10 | 1.20 |
| trans-4-tert-butyl cyclohexanol | 0.50 | 0.90 | 1.50 |
| Sodium dodecyl sulfate | 1.30 | 1.30 | 1.30 |
| Dist. water | to 100.00 | to 100.00 | to 100.00 |

Formulation Example 13: Dental cream against sensitive teeth

| | I (%) | II (%) | III (%) |
|---|---|---|---|
| Na carboxymethylcellulose | 0.70 | 0.70 | 0.70 |
| Xanthan gum | 0.50 | 0.50 | 0.50 |
| Glycerin | 15.00 | 15.00 | 15.00 |
| Sorbitol 70%, in water | 12.00 | 12.00 | 12.00 |
| K-nitrate | 5.00 | 5.00 | 5.00 |
| Na monofluorophosphate | 0.80 | 0.80 | 0.80 |
| PHB methyl ester | 0.15 | 0.15 | 0.15 |
| PHB propyl ester | 0.05 | 0.05 | 0.05 |
| Na saccharinate | 0.20 | 0.20 | 0.20 |
| Peppermint flavor PF1 | 1.00 | 1.00 | 1.00 |
| trans-4-tert-butyl cyclohexanol | 0.50 | 0.90 | 1.50 |
| Ca-carbonate | 35.00 | 35.00 | 35.00 |
| Silicon dioxide | 1.00 | 1.00 | 1.00 |
| Sodium dodecyl sulfate (SDS) | 1.50 | 1.50 | 1.50 |
| Dist. water | to 100.00 | to 100.00 | to 100.00 |

Formulation Example 14: Ready-to-use mouthwash with fluoride

| | I (%) | II (%) | III (%) |
|---|---|---|---|
| Ethanol | 7.00 | 7.00 | 7.00 |
| Glycerin | 12.00 | 12.00 | 12.00 |
| Na fluoride | 0.05 | 0.05 | 0.05 |
| Pluronic F-127 ® (BASF, surface-active substance) | 1.40 | 1.40 | 1.40 |
| Na phosphate buffer pH 7.0 | 1.10 | 1.10 | 1.10 |
| Sorbic acid | 0.20 | 0.20 | 0.20 |
| Na saccharinate | 0.10 | 0.10 | 0.10 |
| Cinnamon/menthol aroma | 0.15 | 0.15 | 0.15 |
| trans-4-tert-butyl cyclohexanol | 0.425 | 0.65 | 0.90 |
| Dyestuff | 0.01 | 0.01 | 0.01 |
| Dist. water | to 100 | to 100 | to 100 |

Formulation Example 15: Sugar-free chewing gum

| | I (%) | II (%) | III (%) |
|---|---|---|---|
| Chewing gum base | 30.00 | 30.00 | 30.00 |
| Sorbitol, powder | Ad 100.00 | Ad 100.00 | Ad 100.00 |
| Palatinite | 9.50 | 9.50 | 9.50 |
| Xylitol | 2.00 | 2.00 | 2.00 |
| Mannitol | 3.00 | 3.00 | 3.00 |
| Aspartame | 0.10 | 0.10 | 0.10 |
| Acesulfame K | 0.10 | 0.10 | 0.10 |
| Emulgum/emulsifier | 0.30 | 0.30 | 0.30 |
| Sorbitol 70%, in water | 14.00 | 14.00 | 14.00 |
| Glycerin | 1.00 | 1.00 | 1.00 |
| Peppermint flavor PF1 | 1.50 | 1.50 | 1.50 |
| trans-4-tert-butyl cyclohexanol | 0.50 | 0.90 | 1.50 |

Formulation Example 16: Gelatine capsules for direct consumption

| | I (wt. %) | II (wt. %) | III (wt. %) |
|---|---|---|---|
| Gelatine shell: | | | |
| Glycerin | 2.014 | 2.014 | 2.014 |
| Gelatine 240 Bloom | 7.91 | 7.91 | 7.91 |
| Sucralose | 0.065 | 0.065 | 0.065 |
| Allura Red | 0.006 | 0.006 | 0.006 |
| Brilliant Blue | 0.005 | 0.005 | 0.005 |

|                                | I (wt. %) | II (wt. %) | III (wt. %) |
|---|---|---|---|
| Core composition:              |           |            |             |
| Plant oil triglyceride         | 82.00     | 74.00      | 60.00       |
| Aroma B                        | 7.85      | 15.50      | 28.50       |
| trans-4-tert-butyl cyclohexanol | 0.50     | 0.90       | 1.50        |

Aroma B here had the following composition (data in each case in wt. %):
0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, had a diameter of 5 mm, and the weight ratio of core material to shell material was 90:10. The capsules opened in the mouth within less than 10 seconds and dissolved completely within less than 50 seconds.

Formulation Example 17: Compressed tablets

|                                | I (wt. %) | II (wt. %) | III (wt. %) |
|---|---|---|---|
| Magnesium stearate (as lubricant) | 0.90   | 0.90       | 0.90        |
| Citric acid                    | 0.20      | 0.20       | 0.20        |
| trans-4-tert-butyl cyclohexanol | 0.50     | 0.90       | 1.50        |
| Dextrose                       | Ad 100    | Ad 100     | Ad 100      |

Formulation Example 18: Instant beverage mix

Formulation Example 19: Sugar-Free Instant Beverage Mix

Formulation Example 20: Soja-Fruit Drink

Formulation Example 21: Low-Fat Yoghurt

|                                | 18     | 19    | 20    | 21    |
|---|---|---|---|---|
| trans-4-tert-butyl cyclohexanol | 3.25  | 4.40  | 0.50  | 0.85  |
| Sugar (sucrose)                | Ad 100 |       |       |       |
| Citric acid                    | 4.00   | 33.33 |       |       |
| Trisodium citrate              | 0.26   |       |       |       |
| Tricalcium phosphate           | 0.22   |       |       |       |
| Ascorbic acid (vitamin C)      | 0.24   | 0.44  |       |       |
| Clouding agent and titanium dioxide (E 171) | 0.20 |    |       |       |
| Xanthan gum (E 415)            | 0.072  |       |       |       |
| Sodium carboxy methyl cellulose (E 467) | 0.064 |  |       |       |
| Pectin (E 440)                 | 0.04   |       |       |       |
| Spray-dried lemon and orange flavour, including yellow colorant tartrazine | 0.40 | | | |
| Spray-dried raspberry flavor, including red colorant |   | 11.50 |  |    |
| Maltodextrin (powder)          |        | Ad 100 |      |       |
| Aspartame                      |        | 3.30   |      |       |
| Saccharose                     |        |        | 6.0  | 5.0   |
| Vanilla flavour                |        |        | 0.10 | 0.125 |
| Mixture of fruit juice concentrates |   |        | 45.0 |       |
| Soja powder                    |        |        | 5.0  |       |

|                                | 18     | 19    | 20    | 21    |
|---|---|---|---|---|
| Yoghurt (1.5 wt. % fat)        |        |       |      | Ad 100 |
| Water                          |        |       | Ad 100 |     |

Formulation Examples 22-31: Formulations comprising trans-4-tert-butyl cyclohexanol according to the present invention having a skin irritation-reducing action Formulation Example 22: "Oil-in-water" emulsion with UV-NB-broadband protection Formulation Example 23: "Oil-in-water" emulsion with UV-NB-broadband protection Formulation Example 24: Sun spray with UV-NB-broadband protection with low oil content Formulation Example 25: Skin-lightening balm with UV-A/UV-B protection Formulation Example 26: Skin-lightening aerosol foam with UV-B/UV-A protection Formulation Example 27: Skin-lightening non-aerosol foam Formulation Example 28: Shampoo with skin-lightening properties Formulation Example 29: Skin-lightening hair conditioner with UV-B/UV-A protection Formulation Example 30: Skin-lightening moisturizing cream O/W Formulation Example 31: Skin-lightening face cream O/W The following Fragrance "ROSE" was used in Formulation Examples 22-31:

Fragrance "ROSE": Perfume Oil with Rose Smell

| Component/NAME | Parts by weight |
|---|---|
| Acetophenone, 10% in DPG | 10.00 |
| n-undecanal | 5.00 |
| Aldehyde C14 so-called (peach aldehyde) | 15.00 |
| Allylamylglycolate, 10% in DPG | 20.00 |
| Amyl salicylate | 25.00 |
| Benzyl acetate | 60.00 |
| Citronellol | 80.00 |
| d-limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial (2-methyl-3-(4-tert-butyl-phenyl)propanal) | 60.00 |
| Linalool | 40.00 |
| Methylphenylacetate | 10.00 |
| Phenylethyl alcohol | 275.00 |
| Styrallyl acetate | 20.00 |
| Terpineol | 30.00 |
| Tetrahydrolinalool | 50.00 |
| Cinnamyl alcohol | 10.00 |

| RAW MATERIAL NAME (MANUFACTURER) | INCI | 22 | 23 | 24 | 25 | 26 | 27 | 28 | 29 | 30 | 31 |
|---|---|---|---|---|---|---|---|---|---|---|---|
| Trans-4-tert-butyl cyclohexanol |  | 1.05 | 0.95 |  |  | 0.35 |  | 0.25 |  | 1.25 |  |

-continued

| RAW MATERIAL NAME (MANUFACTURER) | INCI | 22 | 23 | 24 | 25 | 26 | 27 | 28 | 29 | 30 | 31 |
|---|---|---|---|---|---|---|---|---|---|---|---|
| Trans-4-tert-butyl cyclohexanol as part of CC-2 according to Example 2 | | | | 3.0 | | | | | 1.20 | | 2.75 |
| Trans-4-tert-butyl cyclohexanol as part of CC-3 according to Example 2 | | | | | | | | 1.15 | | | |
| Trans-4-tert-butyl cyclohexanol as part of CC-4 according to Example 2 | | | | | 1.05 | | | | | | 1.00 |
| Skin lightener | | | | | | | | | | | |
| 4-(1-Phenylethyl)-1,3-benzenediol | | 3.0 | 0.05 | 0.2 | 1.0 | 0.5 | — | 0.5 | 0.2 | | 0.5 |
| 4-Butylresorcinol | | | 0.05 | | | | | | | 1.0 | |
| beta-Arbutin | Arbutin | | | | 0.5 | | | | | 0.2 | |
| Kojic acid | Kojic Acid | | | 0.5 | | | | | | | 1.0 |
| Liquorice extract | | | | | | | 2.0 | | | | |
| Mg ascorbyl phosphate | Magnesium Ascorbyl-phosphate | | | | | | | | | 3.0 | |
| Niacinamide | | | | | 1.0 | | | | | | |
| Soya extract | | | 1.0 | | | | | | | | 1.0 |
| Oil components | | | | | | | | | | | |
| Abil 100 ® (Goldschmidt) | Dimethicone | 1.0 | 0.3 | | | | 1.0 | | | 2.0 | 0.3 |
| Cetiol OE (Cognis) | Dicaprylyl Ether | | | | | | | 3.0 | | | |
| Corapan TQ ® (Symrise) | Diethylhexyl 2,6-Naphthalate | | | 2.0 | | | | | | | |
| Dragoxat EH (Symrise) | Ethylhexyl Ethylhexanoate | | | | 1.0 | 1.0 | | | | | |
| Isoadipate (Symrise) | Diisopropyl Adipate | | | | | 1.0 | | | | | |
| Isopropyl myristate (Symrise) | Isopropyl Myristate | | | | | | | | | | 4.0 |
| Isodragol (Symrise) | Triisononanoin | | | | | | | | | 6.0 | |
| Neutral oil (Symrise) | Caprylic/Capric/Triglyceride | 4.0 | 2.0 | | | 2.0 | | | | | |
| Paraffin oil | Mineral Oil | | | | | | | | | | 4.0 |
| PCL Liquid 100 (Symrise) | Cetearyl Octanoate | 4.0 | 3.0 | | | | | | 3.0 | | 4.0 |
| Tegosoft TN ® (Goldschmidt) | C12-C15 Alkyl Benzoate | | | | 4.0 | 2.0 | | | | | |
| Further ingredients | | | | | | | | | | | |
| Arlypon F | Laureth-2 | | | | | | | 2.0 | | | |
| alpha-Bisabolol (Symrise) | Bisabolol | | | 0.1 | | 0.2 | 0.1 | 0.1 | 0.1 | | |
| 1,3-Butylene glycol | 1,3-Butylene Glycol | | | 3.0 | | | | | | | |
| Carbopol 2050 ® (B.F. Goodrich) | Carbomer | | | 0.2 | | 0.5 | 0.1 | | | | |
| Ceramid Bio 391 (Symrise) | Ceramide | 0.3 | | | | | | | | | 0.1 |
| Citric Acid | Citric Acid | | | | | | | | 0.1 | 0.3 | |
| Copherol 1250 ® (Cognis) | Tocopherol Acetate | | | 0.5 | | 0.5 | 0.5 | 0.5 | | | |
| Crinipan ® AD (Symrise) | Climbazole | | | | | | | | 0.5 | | |
| Dehyquart SP | Quaternium-52 | | | | | | | | 0.5 | | |
| Dehyton K | Cocamidopropyl Betaine | | | | | | | | 12.0 | | |
| Dow Corning ® 193 (Dow Corning) | Dimethicone Polyol | | | 1.0 | | | | | | | |
| D-Panthenol (BASF) | Panthenol | | | 0.5 | | | 0.5 | 0.4 | | | |
| Dragocid Liquid (Symrise) | Phenoxyethanol (and) Methylparaben (and) Ethylparaben (and) Butylparaben (and) Propylparaben (and) Isobutylparaben | 0.8 | | 0.8 | 0.8 | 0.8 | 0.8 | 0.8 | 0.5 | 0.8 | 0.8 |

-continued

| RAW MATERIAL NAME (MANUFACTURER) | INCI | 22 | 23 | 24 | 25 | 26 | 27 | 28 | 29 | 30 | 31 |
|---|---|---|---|---|---|---|---|---|---|---|---|
| Dragophos S (Symrise) | Sodium Dihydroxycetyl Phosphate | | | | | | | | | 2.0 | |
| Dracorin CE | Glyceryl Stearate/Citrate | | | | | | | | | 1.0 | |
| Dracorin GMS (Symrise) | Glyceryl Stearate | 2.0 | 2.0 | | | 2.0 | | | | 2.0 | 3.0 |
| Dracorin 100 s.e. P (Symrise) | Glyceryl Stearate, PEG-100 Stearate | 3.0 | | | | | | | | | 8.0 |
| Edeta BD ® (BASF) | Disodium EDTA | 0.1 | 0.1 | | 0.1 | 0.1 | 0.1 | | | | |
| Emulgin B2 ® (Cognis) | Ceteareth-20 | 1.0 | | | | | | | 0.7 | | |
| Emulsiphos (Symrise) | Potassium Cetylphosphate, Hydrogenated Palm Glycerides | | 1.5 | | | 1.5 | | | | | |
| Ethanol (96%) | Ethyl Alcohol | | | 13.0 | 5.0 | | | | | | |
| Extrapon Aloe Vera (Symrise) | | | | 1.0 | | | | | | | |
| Extrapon Kamille (Symrise) | | | | 1.0 | | | | | | | |
| Extrapon Hamamelis (Symrise) | | | | 1.0 | | | | | | | |
| Frescolat ML | Menthyl Lactate | | | | 0.5 | | | | | | |
| Glycerol 99% | Glycerin | 3.0 | | 4.5 | | 3.0 | 4.0 | | | | |
| Hydrolite-5 (Symrise) | Pentylene Glycol | | | | 4.5 | | 5.0 | | | 3.0 | |
| Keltrol T ® (Kelco) | Xanthan Gum | | 0.2 | 0.2 | 0.3 | | | | | | |
| Lanette E ® (Cognis) | Sodium Cetearyl Sulfate | | 0.7 | | | | | | | | |
| Lanette O ® (Cognis) | Cetaeryl Alcohol | 1.1 | | | | | | | 2.5 | | |
| Lanette 16 ® (Cognis) | Cetyl Alcohol | | 1.2 | | | 0.5 | | | | | 2.0 |
| Lanette 18 (Care Chemicals) | Stearyl Alcohol | | | | | | | | | 4.5 | |
| Lara Care A-200 (Rahn) | Galactoarabinan | | | | | | | 0.2 | | | |
| NaOH 10% aq. Solution | Sodium Hydroxide | | 2.8 | | 2.2 | 2.9 | 0.6 | | | | 0.2 |
| Natrosol 250 HHR (Aqualon) | Hydroxymethyl Cellulose | 0.3 | | | | | | | | | |
| Neo Heliopan ® AP (Symrise), 15% as sodium salt | Disodium Phenyl-dibenzimidazole Tetra-sulfonate | | 22.0 | | | | | | | | |
| Neo Heliopan ® AP (Symrise), 10% aq. solution neutralized with NaOH | Disodium Phenyl-dibenzimidazole Tetra-sulphonate | | | | 22.0 | | | | | | |
| Neo Heliopan ® AV (Symrise) | Ethylhexyl Methoxy-cinnamate | | | | 5.0 | 6.0 | 2.0 | | | | |
| Neo Heliopan ® BB (Symrise) | Benzophenone-3 | | 1.0 | | | | | | | | |
| Neo Heliopan ® 303 (Symrise) | Octocrylene | 7.0 | | | | | | | | | |
| Neo Heliopan ® 357 (Symrise) | Butyl Methoxydibenzoyl-methane | | 2.0 | | 1.5 | 1.5 | 1.5 | 0.5 | 0.5 | | |
| Neo Heliopan ® E 1000 (Symrise) | Isoamyl p-Methoxycinnamate | | | | 5.0 | | 6.0 | | 2.0 | | |
| Neo Heliopan ® HMS (Symrise) | Homosalate | | 5.0 | | | | | | | | |
| Neo Heliopan ® Hydro (15% aq. solution neutralized with NaOH) (Symrise) | Phenylbenzimidazole Sulfonic Acid | | | 33.3 | 10.0 | 13.3 | | 3.3 | | | |
| Neo Heliopan ® MA (Symrise) | Menthyl Anthranilate | 3.0 | | | | | | | | | |
| Neo Heliopan ® MBC (Symrise) | 4-Methylbenzylidene Camphor | | | | 2.0 | 4.0 | 3.0 | | | | |
| Neo Heliopan ® OS (Symrise) | Ethylhexyl Salicylate | 1.0 | | | | | | | | | |

-continued

| RAW MATERIAL NAME (MANUFACTURER) | INCI | 22 | 23 | 24 | 25 | 26 | 27 | 28 | 29 | 30 | 31 |
|---|---|---|---|---|---|---|---|---|---|---|---|
| Neo PCL wssl. N (Symrise) | Trideceth-9, PEG-5 Ethylhexanoate | | | 1.0 | 1.5 | | | 1.5 | | | |
| Fragrance "ROSE" (Symrise) | Perfume (Fragrance) | 0.3 | 0.3 | 0.3 | 0.3 | 0.4 | 0.2 | 0.5 | 0.4 | 0.3 | 0.3 |
| Pemulen TR 2 (Novion) | Acrylates/C10-30 Alkyl Acrylate Crosspolymer | | | | | | 0.2 | | | | |
| Polymer JR 400 | Polyquaternium-10 | | | | | | | | 0.4 | | |
| 1,2-Propylene glycol | Propylene Glycol | | | | | | | | | | 5.0 |
| Simagel M | Quaternium-18 Hectorite | 1.0 | | | | | | | | | |
| Solubilizer (Symrise) | PEG 40 Hydrogenated Castor Oil, Trideceth-9, Propylene Glycol, Water | | | | | | | | 3.0 | | |
| Symdiol 68 | 1,2-Hexanediol, Caprylylglycol (1:1) | | 0.5 | | | | | | | | 1.0 |
| Texapon N 70 (Cognis) | Sodium Laureth Sulfate | | | | | | | 0.5 | | | |
| Texapon NSO BZ (Cognis) | Sodium Laureth Sulfate | | | | | | | | 27.0 | | |
| Zink Oxide neutral (Symrise) | Zinc Oxide | 5.0 | | | | | | | | | |
| Veegum ultra ® (Vanderbilt) | Magnesium Aluminium Sulfate | 1.0 | | | | | | | | | |
| Vitamin A Palmitate | Retinyl Palmitate | | | | | 0.1 | | | | 0.1 | |
| Witch Hazel Distillate (Symrise) | Hamamelis Virginiana (Witch Hazel) | | | | | | | | 1.0 | | |
| Water, dist. | Aqua (Water) | ad 100 | ad 100 | ad 100 | ad 100 | ad 100 | ad 100 | ad 100 | ad 100 | ad 100 | ad 100 |

Formulation Example 32: Deodorant sticks

| Component/NAME | A % by weight | B % by weight |
|---|---|---|
| Sodium stearate | 8.00 | 8.00 |
| PPG-3 Myristyl ether | 70.00 | 70.00 |
| 1,2-propylene glygol | 10.00 | 10.00 |
| 1,1-dimethyl-3-phenylpropanol | 0.20 | 0.25 |
| 2-butyloctanoic acid | — | 0.20 |
| Trans-4-tert-butyl cyclohexanol | 0.75 | 0.90 |
| Fragrance "WHITE" | 0.55 | — |
| Fragrance "ROSE" | — | 0.65 |
| Water | Ad 100 | Ad 100 |

Formulation Example 33: Microemulsion gels

| Component/NAME | I (wt. %) | II (wt. %) |
|---|---|---|
| Glycerin isostearate | 1.80 | 2.00 |
| Octoxyglycerin | 1.00 | 0.80 |
| Ceteareth-15 | 5.20 | 5.00 |
| PEG-150 Distearate | 1.00 | 1.00 |
| Aluminium chlorohydrate | 5.00 | 5.00 |
| Isotridecylisononanoate | 3.30 | 3.50 |
| Cyclomethicone | 6.60 | 6.40 |
| Trans-4-tert-butyl cyclohexanol as part of CC-2 according to Example 2 | 1.95 | — |
| Trans-4-tert-butyl cyclohexanol as part of CC-4 according to Example 2 | | 2.45 |
| Fragrance "WHITE" | 0.55 | — |
| Fragrance "ROSE" | — | 0.60 |
| Water | Ad 100 | Ad 100 |

Formulation Example 34: Antiperspirant formulations

| Component/NAME | I (wt. %) | II (wt. %) |
|---|---|---|
| Reach AZP-908 SUF | 24.00 | 22.00 |
| Cyclomethicone (Pentamer) | Ad 100 | Ad 100 |
| Polydecene (Silkflo 364 NF) | 17.50 | 20.00 |
| Neo Helipan OS (ethylhexyl salicylate, Symrise) | 2.50 | 1.00 |
| L-Menthyl lactate (Frescolate ML, Symrise) | 0.25 | — |
| Polyethylene | 3.00 | 3.00 |
| Hydrogenated caster oil | 2.00 | 2.00 |
| Promyristyl PM-3 | 7.00 | 7.00 |
| PEG-8 Distearate | 3.00 | 3.00 |
| Silicon dioxide (Cab-O-Sil M-5) | 1.00 | 1.00 |
| Stearyl alcohol | 15.00 | 10.00 |
| Octyldodecanol | — | 8.00 |
| Trans-4-tert-butyl cyclohexanol | 0.80 | 1.05 |
| Fragrance "WHITE" | 0.75 | — |
| Fragrance "ROSE" | — | 0.80 |

Formulation Example 35: Suspension sticks

| Component/NAME | I (wt. %) | II (wt. %) | III (wt. %) |
|---|---|---|---|
| Stearyl alcohol | 20.00 | 20.00 | 20.00 |
| Cyclomethicone | Ad 100 | Ad 100 | Ad 100 |
| PPG-14 Butylether | 2.00 | 2.00 | 2.00 |
| Hydrogenated caster oil | 1.00 | 1.00 | 1.00 |
| Talc | 2.00 | 2.00 | 2.00 |
| Aluminium chlorohydrate, powder | 20.00 | 20.00 | 20.00 |
| Triclosan ® (5-chloro-2-(2,4-dichlorophenoxy)phenol) | 0.30 | — | 0.30 |
| Ethylhexylglycerin (Octoxyglycerin) | 0.50 | 0.80 | 0.50 |
| 1,1-Dimethyl-3-phenylpropanol | 0.30 | 0.40 | 0.35 |
| Anis alcohol | — | — | 0.15 |

-continued

| Component/NAME | I (wt. %) | II (wt. %) | III (wt. %) |
|---|---|---|---|
| Trans-4-tert-butyl cyclohexanol | 0.55 | 0.85 | 1.10 |
| Fragrance "WHITE" | 0.55 | — | 0.25 |
| Fragrance "ROSE" | — | 0.70 | 0.45 |

Formulation Example 36: Deodorant sprays

| Component/NAME | I (wt. %) | II (wt. %) | III (wt. %) |
|---|---|---|---|
| PEG-40-hydrogenated castor oil | 3.00 | 3.00 | 3.00 |
| Ethylhexylglycerin (Octoxyglycerin) | 0.80 | 0.80 | 0.80 |
| Ethanol | 40.00 | 40.00 | 40.00 |
| Citrate buffer | 0.50 | 0.50 | 0.50 |
| 1,2-Hexanediol/1,2-octanediol (1:1) | — | 0.25 | 0.35 |
| Phenoxyethanol | 0.25 | 0.35 | — |
| Triclosan ® (5-chloro-2-(2,4-dichlorophenoxy)phenol) | 0.25 | — | — |
| 2-Benzylheptan-1-ol (Jasmol) | — | 0.05 | 0.15 |
| Trans-4-tert-butyl cyclohexanol | 0.45 | 0.65 | 0.80 |
| Fragrance "WHITE" | 0.55 | — | 0.25 |
| Fragrance "ROSE" | — | 0.70 | 0.45 |
| Water | Ad 100 | Ad 100 | Ad 100 |

Formulation Example 37: Recrystallization stability test in cosmetic emulsions

| | INCI | I (wt. %) | II (wt. %) | III (wt. %) | IV (wt. %) | V (wt. %) |
|---|---|---|---|---|---|---|
| Emulsiphos | Potassium Cetyl Phosphate. Hydrogenated Palm Glycerides | 1.3 | 1.3 | 2.0 | 1.8 | 2.0 |
| Cutina PES | Glyceryl Stearate | 2.0 | 2.0 | 2.0 | 2.0 | 2.0 |
| Lanette O | Cetearyl Alcohol | 3.5 | 3.5 | 3.5 | 3.5 | 3.5 |
| EDTA BD | Disodium EDTA | 0.1 | 0.1 | 0.1 | 0.1 | 0.1 |
| Neo Heliopan BB | Benzophenone-3 | 0.5 | 0.5 | 0.5 | 0.5 | 0.5 |
| Caprylic/capric triglycerides | Caprylic/Capric Triglyceride | 3.0 | 5.0 | 5.0 | 5.0 | 15.0 |
| Coranpan TQ | Diethylhexyl 2,6-Naphthalate | — | 10.0 | — | — | — |
| Eutanol G 16 | Hexyldecanol | — | — | 10.0 | — | — |
| Finsolv TN | C12-15 Alkyl Benzoate | — | — | — | 10.0 | — |
| Dragoxat 89 | Ethylhexyl Isononanoate | 4.0 | — | — | — | — |
| Isodragol | Triisononanoin | 3.0 | — | — | — | — |
| PCL-Solid | Stearyl Heptanoate, Stearyl Caprylate | 1.0 | — | — | — | — |
| Dragosantol 100 | Alpha-Bisabolol | 0.2 | 0.2 | 0.2 | 0.2 | 0.2 |
| Vitamin E Acetate | Tocopheryl Acetate | 0.5 | 0.5 | 0.5 | 0.5 | 0.5 |
| Keltrol RD | Xanthan Gum | 0.2 | — | 0.2 | 0.2 | 0.2 |
| Benecel | Hydroxypropyl methyl cellulose | — | 1.0 | — | — | 1.0 |
| Trans-4-tert-butyl cyclohexanol | | 0.5 | 0.75 | 1.0 | 1.0 | 1.2 |
| Water | Water (aqua) | Ad 100 | Ad 100 | Ad 100 | Ad 100 | Ad 100 |
| Hydrolite-5 | Pentylene Glycol (1,2-pentanediol) | 3.0 | 3.0 | 3.0 | 3.0 | 3.0 |
| Glycerin | Glycerin | 3.0 | 3.0 | 3.0 | 3.0 | 3.0 |
| SymDiol 68 | 1,2-Hexandiol, Caprylyl Glycol (1:1 (w/w)) | 0.6 | 0.6 | 0.6 | 0.6 | 0.6 |
| Caffeine | Caffeine | 1.0 | — | 3.0 | — | — |
| Citric acid | Citric acid | 0.15 | 0.15 | 0.15 | 0.15 | 0.15 |

The emulsions I to V were stored at 5° C. for 6 months and no crystallization of trans-4-tert-butyl cyclohexanol was observed neither visually nor using microscopic analysis.

The invention claimed is:

1. A cosmetic or pharmaceutical composition for reducing human skin irritation comprising:
   a) 0.1-4.5 wt. % of trans-4-tert-butyl cyclohexanol or a cosmetically or pharmaceutically acceptable salt thereof, based on the total weight of the composition; and
   b) one or more cosmetically or pharmaceutically acceptable carriers;
   wherein if the composition comprises cis-4-tert-butyl cyclohexanol, the weight ratio of the trans-4-tert-butyl cyclohexanol to the cis-4-tert-butyl cyclohexanol is at least 90:10.

2. The composition according to claim 1, wherein the one or more cosmetically acceptable carriers b) are selected from the group consisting of
   (i) alkane diols having 3 to 10 carbon atoms,
   (ii-1) esters having 6 to 36 carbon atoms,
   (ii-2) branched and unbranched alkyl or alkenyl alcohols, and
   (ii-3) branched and unbranched hydrocarbons and waxes, cyclic or linear silicone oils and dialkyl ethers having 6 to 24 carbon atoms.

3. The composition according to claim 1, further comprising at least one fragrance.

4. The composition according to claim 1, further comprising at least one additional active ingredient that provides a benefit to the skin.

5. The composition according to claim 4, wherein the at least one additional active ingredient is selected from the group consisting of:
- extracts or fractions from camomile, Aloe vera, oats, calendula, arnica, honeysuckle, rosemary, witch hazel, ginger or Echinacea;
- alpha-bisabolol, gingerols, shogaols, gingerdiols, dehydrogingerdiones, paradols, natural avenanthramides, non-natural avenanthramides, boswellic acid, phytosterols, glycyrrhizin, or licochalcone A; and
- urea, hyaluronic acid, allantoin, panthenol, lanolin, alpha-hydroxy acids, or vitamin E or derivatives.

6. The composition according to claim 1, wherein the composition is selected from the group consisting of a cosmetic product for treatment, protection, care and cleansing of the skin and/or hair and a make-up product.

7. A concentrated composition comprising
5 to 55 wt. % trans-4-tert-butyl cyclohexanol; and
at least one diol having 3 to 10 carbon atoms;
wherein if the composition comprises cis-4-tert-butyl cyclohexanol, the weight ratio of the trans-4-tert-butyl cyclohexanol to the cis-4-tert-butyl cyclohexanol is at least 90:10.

8. A cosmetic formulation or medicament comprising the composition according to claim 7.

9. The cosmetic composition according to claim 1, wherein the one or more cosmetically acceptable carriers are not water or ethanol.

10. The composition according to claim 2, wherein the one or more cosmetically acceptable carriers b) are selected from the group consisting of
(i) 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, or dipropylene glycol;
(ii-1) diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, $C_{12-15}$-alkyl benzoates, cetyl palmitate, triethyl citrate, triacetin, benzyl benzoate, benzyl acetate, or vegetable oils and triglycerides;
(ii-2) decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, or octyldodecanol and cetearyl alcohol and behenyl alcohol; and
(ii-3) jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane or poly(methyl-phenyl siloxane).

11. The composition according to claim 3, further comprising at least one fragrance having a $C_{log} P$ value of at least 3.

12. The composition according to claim 3, further comprising at least one fragrance selected from the group consisting of: alpha-amyl cinnamic aldehyde, alpha-hexyl cinnamic aldehyde, 2-phenoxyethylisobutyrate, methyl dihydrojasmonate, 4,6,6,7,8,8-hexamethyl-1,3,4,6,7,8-hexahydrocyclopenta[g]benzopyran, benzylsalicylate, 2-methyl-3-(4-tert-butyl-phenyl)propanal, 4,7-methano-3a,4,5,6,7,7a-hexahydro-5-indenyl acetate and/or 4,7-methano-3a,4,5,6,7,7a-hexahydro-6-indenyl acetate, styrallyl acetate, octahydro-2,3,8,8-tetramethyl-2-acetonaphthone and/or 2-acetyl-1,2,3,4,6,7,8-octahydro-2,3,8,8-tetramethylnaphthaline, hexylsalicylate, 4-tert.-butylcyclohexyl acetate, 2-tert.-butylcyclohexyl acetate, alpha-ionone, 4-(4-hydroxy-4-methylpentyl)-3-cyclohexene carboxaldehyde, (E)- and/or (Z)-3-methylcyclopentadec-5-enone, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl) ethanone, ethylene brassylate, 2-ethyl-4-(2,2,3-trimethyl-3-cyclopenten-1-yl)-2-buten-1-ol, alpha-Santalol, 2,2-dimethyl-3-(3-methylphenyl)-propanol (Majantol), allyl heptanoate, 4-methylacetophenone, (4aR,5R,7aS,9R)-octahydro-2,2,5,8,8,9a-hexamethyl-4H-4a,9-methanoazuleno (5,6-d)-1,3-dioxol), 1-(2,2,6-trimethylcyclohexyl)hexan-3-ol, benzylacetone, methyl cinnamate, and 3a,6,6,9a-tetramethyldodecahydronaphtho[2,1-b]furan.

13. The composition according to claim 4, wherein the additional active ingredient that provides a benefit to the skin is selected from the group consisting of anti-inflammatory agents, physiological cooling agents, compounds that alleviate itching and compounds that alleviate reddening, wherein the active is suitable for cosmetic and/or dermatological applications.

14. The concentrated composition according to claim 7, comprising 7.5 wt. % or more of an alkane diol selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, and dipropylene glycol.

15. The composition according to claim 1, wherein if the composition comprises cis-4-tert-butyl cyclohexanol, the weight ratio of the trans-4-tert-butyl cyclohexanol to the cis-4-tert-butyl cyclohexanol is at least 95:5.

16. A cosmetic or pharmaceutical composition for reducing human skin irritation comprising:
a) 0.1-4.5 wt. % of trans-4-tert-butyl cyclohexanol or a cosmetically or pharmaceutically acceptable salt thereof, based on the total weight of the composition, wherein if the composition comprises cis-4-tert-butyl cyclohexanol, the weight ratio of the trans-4-tert-butyl cyclohexanol to the cis-4-tert-butyl cyclohexanol is at least 95:5;
b) one or more cosmetically or pharmaceutically acceptable carriers selected from the group consisting of:
(i) an alkane diol having 3 to 10 carbon atoms,
(ii-1) an ester having 6 to 36 carbon atoms,
(ii-2) a branched or unbranched alkyl or alkenyl alcohol, and
(ii-3) a branched or unbranched hydrocarbon, a wax, a cyclic or linear silicone oil, or an ether having 6 to 24 carbon atoms; and
c) at least one fragrance having a $C_{log} P$ value of at least 3.

17. The composition according to claim 16, further comprising:
- (d) an additional active ingredient suitable for cosmetic application to the skin selected from the group consisting of an anti-inflammatory agent, a physiological cooling agent, a compound that alleviates itching, and a compound that alleviates reddening.

18. The composition according to claim 16 comprising (i) an alkane diol having 3 to 10 carbon atoms selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, and dipropylene glycol.

19. A method for reducing human skin irritation comprising applying to the skin of a human an effective amount of a cosmetic composition according to claim 1.

* * * * *